United States Patent [19]
Bhagwat et al.

[11] Patent Number: 6,030,969
[45] Date of Patent: *Feb. 29, 2000

[54] 5,6,7-TRISUBSTITUTED-4-AMINOPYRIDO[2,3-D] PYRIMIDINE COMPOUNDS

[75] Inventors: Shripad S. Bhagwat, Lake Bluff; Richard J. Perner, Gurnee; Yu-Gui Gu, Grayslake, all of Ill.

[73] Assignee: Abbott Laboratories, Abbot Park, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 09/058,324

[22] Filed: Apr. 9, 1998

Related U.S. Application Data
[60] Provisional application No. 60/043,252, Apr. 16, 1997.

[51] Int. Cl.$^7$ ........................ C07D 471/04; A61K 31/505
[52] U.S. Cl. ........................ 514/234.5; 514/258; 544/117; 544/279
[58] Field of Search ................................ 514/234.5, 258; 544/117, 279

[56] References Cited

U.S. PATENT DOCUMENTS

| | | | |
|---|---|---|---|
| 5,026,851 | 6/1991 | Taylor et al. | 544/279 |
| 5,034,393 | 7/1991 | Hackler et al. | 514/258 |
| 5,736,547 | 4/1998 | Gangjee | 514/258 |
| 5,821,244 | 10/1998 | Schaper et al. | 514/248 |

FOREIGN PATENT DOCUMENTS

| | | |
|---|---|---|
| 9519774 | 7/1995 | WIPO . |

OTHER PUBLICATIONS

Bennett, L. L., et al., "Purine Ribonucleoside Kinase Activity and Resistance to Some Analogs of Adenosine", *Mol. Pharmacol.*, 2:432–443 (1966).
Burnstock, G., "A Basis for Distinguishing Two Types of Purinergic Receptor", *Cell Membrane Receptors for Drugs and Hormones*, Raven Press, NY (1978).
Caldwell, I. C., et al., "Resistance to Purine Ribonucleoside Analogues in an Ascites Tumor", *Canadian Journ. Of Biochemistry*, 45:735–744 (1967).
Corradetti, R., et al., "Adenosine Decreases Aspartate and Glutamate Release from Rat Hippocampal Slices", *European Journ. Of Pharm.*, 104:19–26 (1984).
Cronstein, B. N., "Adenosine, an endogenous anti–inflammatory agent", *Journ. Of Applied Physiology*, 76:5–13 (1994).
Davies, L. P., et al., "Halogenated Pyrrolopyrimidine Analogues of Adenosine from Marien Organisms: Pharmacological Activities and Potent Inhibition of Adenosine Kinase", *Biochemical Pharmacology*, 33(3):347–355 (1984).
Dragunow, M., "Adenosine: the brain's natural anticonvulsant?", *Trends in Pharmacological Sciences*, 7:128–130 (1986).
Firestein, G.S., et al., Selectin–Mediated Anti–inflammatory Effects of Adenosine (ADO) And an ADO Kinase Inhibitor, *Arthritis and Rheumatism*, 36:48s (1993).
Fredholm, B. B., et al., "VI. Nomenclature and Classification of Purinoceptors", *Pharmacological Reviews*, 46(2):143–156 (1994).
Gupta, A., et al., "Fluorine containing Biologically Active Agents: Synthesis of some New Pyrimidine Derivatives", *J. Indian Chem. Soc.*, 71:635–636 (1994).
Hagen, V., et al., "Potentielle Kardiotonika", *Pharmazie*, 46:531–532 (1991).
Hershfield & Kredich, "Resistance of an adenosine kinase–deficient human lymphoblastoid cell line to effects of deoxyadenosine on growth, S–adenosyl–homocysteine hydrolase inactivation, and dATP accumulation", *Proc. Natl. Acad. Sci. USA*, 77(7):4292–4296 (1980).
Hurlbert, B. S., et al., "Studies on Condensed Pyrimidine Systems, XXV, 2,4–Diaminopyrido[2,3–d]pyrimidines. Biological Data", *Journ. Of Medicinal Chemistry*, 11:711–717 (1968).
Kredich & Hershfield, "Immunodeficiency Diseases Caused by Adenosine Deaminase Deficiency and Purine Nucleoside Phosphorylase Deficiency", *The Metabolic Basis of Inherited Disease*, 6$^{th}$ed., McGraw Hill, NY, pp. 1045–1075 (1989).
Londos, C., et al., "Subclasses of external adenosine receptors", *Proc. Natl. Acad. Sci. USA*, 77(5):2551–2554 (1980).
Miller & Hsu, "Adenosine Receptors: Mechanisms of Action and Physiological Role in CNS", *Journal of Neurotrauma*, 9:563S–577S (1992).
Miller, et al., "Adenosine Kinase from Rabbit Liver", *The Journ. Of Biol. Chem.*, 254(7):2339–2345, (1979).

(List continued on next page.)

*Primary Examiner*—Mukund J. Shah
*Assistant Examiner*—Deepak R. Rao
*Attorney, Agent, or Firm*—Robert A. Miller

[57] ABSTRACT

A compound having the formula

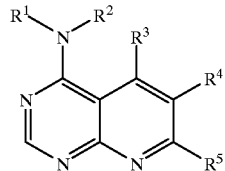

wherein $R^1$, $R^2$, $R^3$, $R^4$ and $R^5$ are defined, a method for inhibiting adenosine kinase by administering a compound thereof, a pharmaceutical composition comprising a therapeutically effective amount of a compound thereof above in combination with a pharmaceutically acceptable carrier, a method of treating cerebral ischemia, epilepsy, pain, nociperception, inflammation and sepsis in a mammal in need of such treatment, comprising administering to the mammal a therapeutically effective amount of a compound thereof, and methods for preparation thereof.

16 Claims, No Drawings

OTHER PUBLICATIONS

Moser, G. H., et al., "Turnover of adenosine in plasma off human and dog blood", *Amer. Journ. Of Physiology*, 25:C799–C806 (1989).

Mullane & Williams, "Adenosine and Cardiovascular Function", *Adenosine and Adenosine Receptors*, Humana Press, NJ, pp. 289–334 (1990).

Prakash, L., et al., "Novel condensation products of 2–amino–3–cyano–4,6–disubstituted pyridine with urea, thiourea, formanide and carbon disulfide", *Pharmazie*, 48:221–222 (1993).

Robins, R. K., et al., "Studies on Condensed Pyrimidine Systems. XIX. A New Synthesis of Pyrido [2,3–d]pyrimidines. The Condensation of 1,3–Diketones and 3–Ketoaldehydes with 4–Aminopyrimidines", 80:3449–3457 (1958).

Rudolphi, K. A., et al., "Adenosine and Brain Ischemia", *Cerebrovascular and Brain Metabolism Reviews*, 4:346–369 (1992).

Rudolphi, K. A., et al., "Neuroprotective role of adenosine in cerebral ischaemia", *Trends in Pharmacological Sciences*, 13:439–445 (1992).

Sawynok, J., et al., "Classification of adenosine receptors mediating antinociception in the rat spinal cord", *Br. J. Pharmac.*, 88:923–930 (1986).

Sharma, R., et al., "Synthesis of 5,7–disubstituted pyridol [2,3–d]–pyrimidine derivatives and their antibacterial activity", *Indian Journ. Of Chem.*, 31(B):719–720 (1992).

Suttle, D. P., et al., "Pyrazofurin–Resistant Hepatoma Cells Deficient in Adenosine Kinase", *Europ. J. Cancer*, 17:43–51 (1981).

Sweeney, M. I., et al., "Involvement of Adenosine in the Spinal Antinociceptive Effects of Morphine and Noradrenaline[1]", *The Journ. Of Pharm. And Exp. Therapeutics*, 243(2):657–665 (1987).

Victory, P., et al., "Two Step Synthesis of Pyrido[2,3–d] pyrimidines from Acyclic Precursors. Cyclization of 2–Cyanamino–4,6–diphenylpyridine–3–carbonitrile by Hydrogen Halides", *Tetrahedron*, 51(37):10253–10258 (1995).

Williams, M., "Purinoceptors in Central Nervous System Function", *Psychopharmacology: the Fourth Gen. Of Prog.*, 643–655 (1995).

Wotring and Townsend, "Study of the Cytotoxicity and Metabolism of 4–Amino–3–carboxamido–1–(β–D–ribofuranosyl)pyrazolo [3,4–d]pyrimidine Using Inhibitors of Adenosine Kinase and Adenosine Deaminase[1]", *Cancer Research*, 39:3018–3023 (1979).

5,6,7-TRISUBSTITUTED-4-AMINOPYRIDO[2, 3-D] PYRIMIDINE COMPOUNDS

This application is a conversion of copending provisional U.S. patent application Ser. No. 60/043,252, filed Apr. 16, 1997.

TECHNICAL FIELD

The present invention relates a method for inhibiting adenosine kinase by administering 5,6,7-trisubstituted-4-aminopyrido[2,3-d]pyrimidine compounds, to pharmaceutical compositions containing such compounds, as well as novel 5,6,7-trisubstituted-4-aminopyrido[2,3-d]pyrimidine compounds.

BACKGROUND OF THE INVENTION

Adenosine kinase (ATP:adenosine 5'-phosphotransferase, EC 2.7.1.20) is a ubiquitous enzyme which catalyzes the phosphorylation of adenosine to AMP, using ATP, preferentially, as the phosphate source. Adenosine kinase has broad tissue and species distribution, and has been isolated from yeast, a variety of mammalian sources and certain microorganisms. It has been found to be present in virtually every human tissue assayed including kidney, liver, brain, spleen, placenta and pancreas. Adenosine kinase is a key enzyme in the control of the cellular concentrations of adenosine.

Adenosine is a purine nucleoside that is an intermediate in the pathways of purine nucleotide degradation and salvage. Adenosine also has many important physiologic effects, many of which are mediated through the activation of specific ectocellular receptors, termed $P_1$ receptors (Burnstock, in *Cell Membrane Receptors for Drugs and Hormones,* 1978, (Bolis and Straub, eds.) Raven, N.Y., pp. 107–118; Fredholm, et al., *Pharmacol. Rev.* 1994, 46: 143–156).

In the central nervous system, adenosine inhibits the release of certain neurotransmitters (Corradetti, et al., *Eur. J. Pharmacol.* 1984, 104: 19–26), stabilizes membrane potential (Rudolphi, et al., *Cerebrovasc. Brain Metab. Rev.* 1992, 4: 346–360), functions as an endogenous anticonvulsant (Dragunow, *Trends Pharmacol. Sci.* 1986, 7: 128–130) and may have a role as an endogenous neuroprotective agent (Rudolphi, et al., *Trends Pharmacol. Sci.,* 1992, 13: 439–445). Adenosine may play a role in several disorders of the central nervous system such as schizophrenia, anrxiety, depression and Parkinson's disease. (Williams, M., in *Psychopharmacology: The Fourth Generation of Progress*; Bloom, Kupfer (eds.), Raven Press, N.Y., 1995, pp 643–655.

Adenosine has also been implicated in modulating transmission in pain pathways in the spinal cord (Sawynok, et al., *Br. J. Pharmacol.,* 1986, 88: 923–930), and in mediating the analgesic effects of morphine (Sweeney, et al., *J. Pharmacol. Exp. Ther.* 1987, 243: 657–665).

In the immune system, adenosine inhibits certain neutrophil functions and exhibits anti-inflammatory effects (Cronstein, *J. Appl. Physiol.* 1994, 76: 5–13). An AK inhibitor has been reported to decrease paw swelling in a model of adjuvant arthritis in rats (Firestein, et.al., *Arthritis and Rheumatism,* 1993, 36, S48.

Adenosine also exerts a variety of effects on the cardiovascular system, including vasodilation, impairment of atrioventricular conduction and endogenous cardioprotection in myocardial ischemia and reperfusion (Mullane and Williams, in *Adenosine and Adenosine Receptors,* 1990 (Williams, ed.) Humana Press, New Jersey, pp. 289–334). The widespread actions of adenosine also include effects on the renal, respiratory, gastrointestinal and reproductive systems, as well as on blood cells and adipocytes. Adenosine, via its A1 receptor activation on adipocytes, plays a role in diabetes by inhibiting lipolysis [Londos, et al., Proc. Natl. Acad. Sci. USA, 1980, 77, 2551.

Endogenous adenosine release appears to have a role as a natural defense mechanism in various pathophysiologic conditions, including cerebral and myocardial ischemia, seizures, pain, inflammation and sepsis. While adenosine is normally present at low levels in the extracellular space, its release is locally enhanced at the site(s) of excessive cellular activity, trauma or metabolic stress. Once in the extracellular space, adenosine activates specific extracellular receptors to elicit a variety of responses which tend to restore cellular function towards normal (Bruns, *Nucleosides Nucleotides,* 1991, 10: 931–943; Miller and Hsu, *J. Neurotrauma,* 1992, 9: S563–S577). Adenosine has a half-life measured in seconds in extracellular fluids (Moser, et al., *Am. J. Physiol.* 1989, 25: C799–C806), and its endogenous actions are therefore highly localized.

The inhibition of adenosine kinase can result in augmentation of the local adenosine concentrations at foci of tissue injury, further enhancing cytoprotection. This effect is likely to be most pronounced at tissue sites where trauma results in increased adenosine production, thereby minimizing systemic toxicities.

Pharmacologic compounds directed towards adenosine kinase inhibition provide potentially effective new therapies for disorders benefited by the site- and event-specific potentiation of adenosine. Disorders where such compounds may be useful include ischemic conditions such as cerebral ischemia, myocardial ischemia, angina, coronary artery bypass graft surgery (CABG), percutaneous transluminal angioplasty (PTCA), stroke, other thrombotic and embolic conditions, and neurological disorders such as epilepsy, anxiety, schizophrenia, nociperception including pain perception, neuropathic pain, visceral pain, as well as inflammation, arthritis, immunosuppression, sepsis, diabetes and gastrointestinal disfunctions such as abnormal gastrointestinal motility.

A number of compounds have been reported to inhibit adenosine kinase. The most potent of these include 5'-amino-5'-deoxyadenosine (Miller, et al., *J. Biol. Chem.* 1979, 254: 2339–2345), 5-iodotubercidin (Wotring and Townsend, *Cancer Res.* 1979, 39: 3018–3023) and 5'-deoxy-5-iodotubercidin (Davies, et al, *Biochem. Pharmacol.* 1984, 33: 347–355).

Adenosine kinase is also responsible for the activation of many pharmacologically active nucleosides (Miller, et al., *J. Biol. Chem.* 1979, 254: 2339–2345), including tubercidin, formycin, ribavirin, pyrazofurin and 6-(methylmercapto) purine riboside. These purine nucleoside analogs represent an important group of antimetabolites which possess cytotoxic, anticancer and antiviral properties. They serve as substrates for adenosine kinase and are phosphorylated by the enzyme to generate the active form. The loss of adenosine kinase activity has been implicated as a mechanism of cellular resistance to the pharmacological effects of these nucleoside analogs (e.g. Bennett, et al., *Mol. Pharmacol,* 1966, 2: 432–443; Caldwell, et al., *Can. J. Biochem.,* 1967, 45: 735–744; Suttle, et al., *Europ. J. Cancer,* 1981, 17: 43–51). Decreased cellular levels of adenosine kinase have also been associated with resistance to the toxic effects of 2'-deoxyadenosine (Hershfield and Kredich, *Proc. Natl.*

Acad. Sci. USA, 1980, 77: 4292–4296). The accumulation of deoxyadenosine triphosphate (dATP), derived from the phosphorylation of 2'-deoxyadenosine, has been suggested as a toxic mechanism in the immune defect associated with inheritable adenosine deaminase deficiency (Kredich and Hershfield, in *The Metabolic Basis of Inherited Diseases,* 1989 (Scriver, et al., eds.), McGraw-Hill, New York, pp. 1045–1075).

B. S. Hurlbert et al. (*J. Med. Chem.,* 11: 711–717 (1968)) disclose various 2,4-diaminopyrido[2,3-d]pyrimidine compounds having use as antibacterial agents. R. K. Robins et al. (*J. Amer. Chem. Soc.,* 80:3449–3457 (1958)) disclose methods for preparing a number of 2,4-dihydroxy-, 2,4diamino-, 2-amino-4-hydroxy- and 2-mercapto-4-hydroxypyrido[2,3-d]pyrimidine having antifolic acid activity. R. Sharma et al., (*Indian J. Chem.,* 31B: 719–720 (1992)) disclose 4-amino-5-(4-chlorophenyl)-7-(4-nitrophenyl)pyrido[2,3-d]pyrimidine and 4-amino-5-(4-methoxyphenyl)-7-(4-nitrophenyl)pyrido[2,3-d]pyrimidine compounds having antibacterial activity. A. Gupta et al., (*J. Indian Chem. Soc.,* 71: 635–636 (1994)) disclose 4-amino-5-(4-fluorophenyl)-7-(4-fluorophenyl)pyrido[2,3-d]pyrimidine and 4-amino-5-(4-chlorophenyl)-7-(4-fluorophenyl)pyrido[2,3-d] pyrimidine compounds having antibacterial activity. L. Prakash et al., *Pharmazie,* 48: 221–222 (1993)) disclose 4-amino-5-phenyl-7-(4-aminopheny)pyrido[2,3-d]pyrimidine, 4-amino-5-phenyl-7-(4-bromophenyl)pyrido[2,3-d]pyrimidine, 4-amino-5-(4-methoxyphenyl)-7-(4-aminophenyl)pyrido[2,3-d]pyrimidine, and 4-amino-5-(4-methoxyphenyl)-7-(4-bromophenyl)pyrido[2,3-d] pyrimidine compounds having antifungal activity. P. Victory et al., *Tetrahedron,* 51: 10253–10258 (1995)) discloses the synthesis of 4-amino-5,7-diphenylpyrido[2,3-d]pyrimidine compounds from acyclic precursors Bridges et al.(PCT application WO 95/19774, published Jul. 27, 1995) disclose various bicyclic heteroaromatic compounds as having utility for inhibiting tyrosine kinase of epidermal growth factors.

SUMMARY OF THE INVENTION

The present invention provides for 5,6,7-trisubstituted-4-aminopyrido[2,3-d]pyrimidine compounds having utility as adenosine kinase inhibitors. In one aspect, the present invention provides compounds having the formula (I)

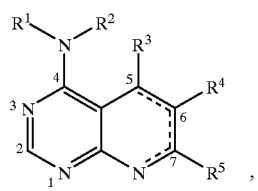
(I)

wherein
$R^1$ and $R^2$ are independently H, loweralkyl, arylalkyl or acyl, or may be taken together with the nitrogen atom to which they are attached to form a 5-to-7 membered ring optionally containing 1–3 additional heteroatoms selected from N, O or S;
$R^3$, $R^4$ and $R^5$ are independently selected from loweralkyl, loweralkenyl, loweralkynyl, lower cycloalkyl, aryl, arylalkyl, heteroaryl, or a heterocyclic group and the dashed lines indicate a double bond is optionally present.

The present invention also relates to a compound of formula II

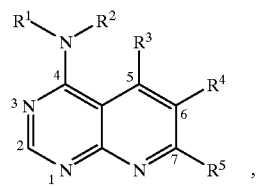
(II)

wherein
$R^1$ and $R^2$ are independently H, loweralkyl, arylalkyl or acyl, or may be taken together with the nitrogen atom to which they are attached to form a 5-to-7 membered ring optionally containing 1–3 additional heteroatoms selected from N, O or S; and
$R^3$, $R^4$ and $R^5$ are independently selected from loweralkyl, loweralkenyl, loweralkynyl, lower cycloalkyl, aryl, arylalkyl, heteroaryl, or a heterocyclic group.

In another aspect, the present invention provides a method for inhibiting adenosine kinase by administering a compound of formula (I) or (II).

In particular, the method of inhibiting adenosine kinase comprises exposing an adenosine kinase to an effective inhibiting amount of a compound of Formula I or II of the present invention. Where the adenosine kinase is located in vivo, the compound is administered to the organism.

In yet another aspect, the present invention provides a pharmaceutical composition comprising a therapeutically effective amount of a compound of Formula I or II above in combination with a pharmaceutically acceptable carrier.

In still another aspect, the present invention provides a method of treating ischemia, neurological disorders, nociperception, inflammation, immunosuppression, gastrointestinal disfunctions, diabetes and sepsis in a mammal in need of such treatment, comprising administering to the mammal a therapeutically effective amount of a compound of Formula I or II of the present invention.

In a preferred aspect, the present invention provides a method of treating cerebral ischemia, myocardial ischemia, angina, coronary artery bypass graft surgery, percutaneous transluminal angioplasty, stroke, thrombotic and embolic conditions, epilepsy, anxiety, schizophrenia, pain perception, neuropathic pain, visceral pain, artritis, sepsis, diabetes and abnormal gastrointestinal motility in a mammal in need of such treatment, comprising administering to the mammal a therapeutically effective amount of a compound of Formula I or II of the present invention.

The present invention also contemplates the use of pharmaceutically acceptable salts and amides of the compounds of Formula I or II.

In another aspect, the present invention provides a process for the preparation of a compound having the formula

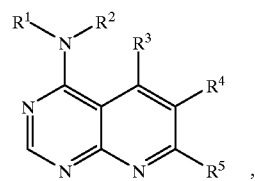
(II)

wherein
$R^1$ and $R^2$ are independently H, loweralkyl, arylalkyl or acyl, or may be taken together with the nitrogen atom to which they are attached to form a 5-to-7 membered ring optionally containing 1–3 additional heteroatoms selected from N, O or S; and R³ and R⁴ are independently selected from loweralkyl, loweralkenyl, loweralkynyl, lower cycloalkyl, aryl, arylalkyl, heteroaryl, or a heterocyclic group; and R⁵ is selected from an aryl, heteroaryl or heterocyclic group; the method comprising (a) reacting an aryl, heteroaryl, or a heterocyclic bromide having the formula R⁵—Br wherein R⁵ is as defined above with a carboxylic acid derivative having the formula R⁴—CH₂—CO—Y, wherein Y is OH or Cl, and R⁴ is loweralkyl, loweralkenyl, loweralkynyl, aryl, arylalkyl, heteroaryl, or a heterocyclic group, with N,O-dimethylhydroxylamine hydrochloride, 1-(3-dimethylaminopropyl)- 3-ethylcarbodiimide or 1-hydroxybenzotriazole hydrate and triethylamine, and isolating a first intermediate compound having the formula R⁵—CO—CH₂—R⁴;

(b) reacting the first intermediate compound having the formula R⁵—CO—CH₂—R⁴, with an aldehyde having the formula R³—CHO, wherein R³ is as defined above, and malononitrile in the presence of an ammonium salt under anhydrous conditions, and isolating a second intermediate compound having the formula

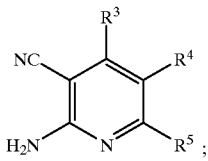

(c) reacting the second intermediate compound with formamide at reflux for from about 1 to about 24 hours, and isolating the compound of formula II.

In still another aspect, the present invention provides a process for the preparation of compounds having the formula

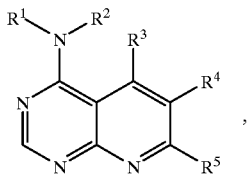

wherein

R¹ and R² are independently H, loweralkyl, arylalkyl or acyl, or may be taken together with the nitrogen atom to which they are attached to form a 5-to-7 membered ring optionally containing 1–3 additional heteroatoms selected from N, O or S; and R³ and R⁴ are independently selected from loweralkyl, loweralkenyl, loweralkynyl, lower cycloalkyl, aryl, arylalkyl, heteroaryl, or a heterocyclic group; and R⁵ is selected from an aryl, heteroaryl or heterocyclic group; with the proviso that not both R¹ and R² are H, the method comprising (a) reacting an aryl, heteroaryl, or a heterocyclic bromide having the formula R⁵—Br with a carboxylic acid derivative having the formula R⁴—CH₂—CO—Y, wherein Y is OH or Cl, and R⁴ is loweralkyl, loweralkenyl, loweralkynyl, aryl, arylalkyl, heteroaryl, or a heterocyclic group, with N,O-dimethylhydroxylamine hydrochloride, 1-(3-dimethylamrinopropyl)-3-ethylcarbodiimide or 1-hydroxybenzotriazole hydrate and triethylamine, and isolating a first intermediate compound having the formula R⁵—CO—R⁴;

(b) reacting the first intermediate compound having the formula R⁵—CO—R⁴, with an aldehyde having the formula R³—CHO, wherein R³ is as defined above, and malononitrile in the presence of an ammonium salt under anhydrous conditions, and isolating a second intermediate compound having the structure

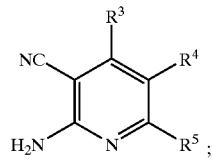

(c) reacting the second intermediate compound with sulfuric acid and heating followed by treatment with triethyl orthoformate at reflux for from about 1 to about 24 hours, and isolating a third intermediate compound having the structure

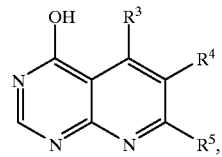

(d) treating the third intermediate compound with a chlorinating agent, and isolating a fourth intermediate product having the formula

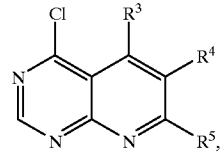

with an amine compound having the formula R¹—NH—R², wherein R¹ and R² are as described above, and isolating the compound of formula II.

In yet another aspect, the present invention provides a process for the preparation of compounds having the formula

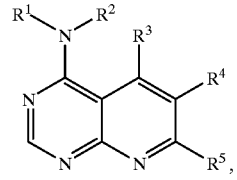

wherein

R¹ and R² are independently H, loweralkyl, arylalkyl or acyl, or may be taken together with the nitrogen atom to which they are attached to form a 5-to-7 membered ring optionally containing 1–3 additional heteroatoms selected from N, O or S; and R³ and R⁴ are independently selected from loweralkyl, loweralkenyl, loweralkynyl, lower cycloalkyl, aryl, arylalkyl, heteroaryl, or a heterocyclic group; and $R^5$ is selected from an aryl, heteroaryl or heterocyclic group; the method comprising (a) reacting an aryl, heteroaryl, or a heterocyclic bromide having the formula $R^5$—Br with a carboxylic acid derivative having the formula $R^4$—$CH_2$—CO—Y, wherein Y is OH or Cl, and $R^4$ is loweralkyl, loweralkenyl, loweralkynyl, aryl, arylalkyl, heteroaryl, or a heterocyclic group, with N,O-dimethylhydroxylamine hydrochloride, 1-(3-dimethylaminopropyl)-3-ethylcarbodiimide or 1-hydroxybenzotriazole hydrate and triethylamine, and isolating a first intermediate compound having the formula $R^5$—CO—$CH_2$—$R^4$;

(b) treating the first intermediate compound having the formula $R^5$—CO—$CH_2$—$R^4$, with a compound having the formula

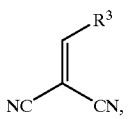

wherein $R^3$ is as described above, at reflux in an alcoholic solvent, and isolating a second intermediate product having the formula

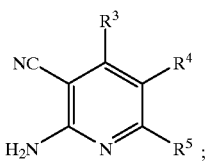

and (c) reacting the second intermediate compound with formamide at reflux for from about 1 to about 24 hours, and isolating the desired product.

In still another aspect, the present invention provides a process for the preparation of compounds having the formula

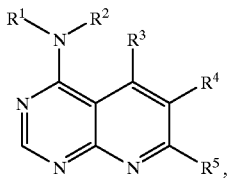

wherein $R^1$ and $R^2$ are independently H, loweralkyl, arylalkyl or acyl, or may be taken together with the nitrogen atom to which they are attached to form a 5-to-7 membered ring optionally containing 1–3 additional heteroatoms selected from N, O or S; and $R^3$ and $R^4$ are independently selected from loweralkyl, loweralkenyl, loweralkynyl, aryl, arylalkyl, heteroaryl, or a heterocyclic group; and $R^5$ is selected from an aryl, heteroaryl or heterocyclic group, with the proviso that not both $R^1$ and $R^2$ are hydrogen, the method comprising (a) reacting an aryl, heteroaryl, or a heterocyclic bromide having the formula $R^5$—Br with a carboxylic acid derivative having the formula $R^4$—$CH_2$—CO—Y, wherein Y is OH or Cl, and $R^4$ is loweralkyl, loweralkenyl, loweralkynyl, aryl, arylalkyl, heteroaryl, or a heterocyclic group, with N,O-dimethylhydroxylamine hydrochloride, 1-(3-dimethylaminopropyl)-3-ethylcarbodiimide or 1-hydroxybenzotriazole hydrate and triethylamine, and isolating a first intermediate compound having the formula $R^5$—CO—$CH_2$—$R^4$;

(b) treating the first intermediate compound having the formula $R^5$—CO—$CH_2$—$R^4$, with a compound having the formula

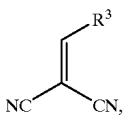

wherein $R^3$ is as described above, at reflux in an alcoholic solvent, and isolating a second intermediate product having the formula

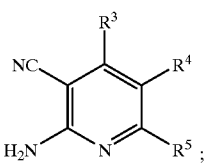

and (c) reacting the second intermediate compound with sulfuric acid and heating followed by treatment with triethyl orthoformate at reflux for from about 1 to about 24 hours, and isolating a third intermediate compound having the structure

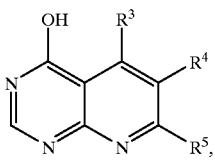

(d) treating the third intermediate compound with a chlorinating agent, and isolating a fourth intermediate product having the formula

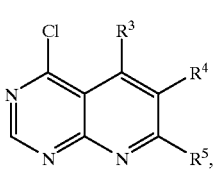

(e) treating the fourth intermediate compound with an amine compound having the formula $R^1$—NH—$R^2$, wherein $R^1$ and $R^2$ are as described above, and isolating the compound of formula II.

The present invention also relates to any of the above processes and an additional process step which reduces or partially reduces the right side double bond(s) to partially saturated or fully saturated species as indicated generically by formula I. The preferred reduction method is via catalytic hydrogenation.

DETAILED DESCRIPTION OF THE INVENTION

The present invention relates to novel 5,6,7-trisubstituted-4-aminopyrido[2,3-d]pyrimidine compounds of Formula (I)

above that are useful in inhibiting adenosine kinase, a method of inhibiting adenosine kinase with such compounds, to pharmaceutical compositions containing such compounds, to a method of using such compounds for inhibiting adenosine kinase, and to novel 5,6,7-trisubstituted-4-aminopyrido[2,3-d]pyrimidine compounds.

The present invention relates to a compound of formula I or II as described above wherein:

$R^1$ and $R^2$ are independently selected from H, loweralkyl, aryl$C_1$–$C_6$alkyl, —C(O)$C_1$–$C_6$alkyl, —C(O)aryl, —C(O)heterocyclic or may join together with the nitrogen to which they are attached to from a 5–7 membered ring optionally containing 1–2 additional heteroatoms selected from O, N or S;

$R^3$, $R^4$ and $R^5$ are independently selected from the group consisting of:
$C_1$–$C_6$alkyl,
$C_2$–$C_6$alkenyl,
$C_2$–$C_6$alkynyl,
$C_3$–$C_8$cycloalkyl,
heteroaryl$C_0$–$C_6$alkyl or substituted heteroaryl$C_0$–$C_6$alkyl,
aryl$C_0$–$C_6$alkyl or substituted aryl$C_0$–$C_6$alkyl,
heteroaryl$C_2$–$C_6$alkenyl or substituted heteroaryl$C_2$–$C_6$alkenyl,
aryl$C_2$–$C_6$alkenyl or substituted aryl$C_2$–$C_6$alkenyl,
heteroaryl$C_2$–$C_6$alkynyl or substituted heteroaryl$C_2$–$C_6$alkynyl,
aryl$C_2$–$C_6$alkynyl or substituted aryl$C_2$–$C_6$alkynyl wherein the 1–4 heteroaryl or aryl substituents are independently selected from
halogen, oxo, cyano$C_1$–$C_6$alkyl, heteroaryl$C_0$–$C_6$alkyl, heterocyclic$C_0$–$C_6$alkyl, $C_1$–$C_6$alkyloxy, $C_1$–$C_6$alkyloxy$C_1$–$C_6$alkyl, aryl$C_0$–$C_6$alkyl, aryl$C_1$–$C_6$alkyloxy, $R^6R^7NC(O)$, cyano, $C_2$–$C_6$alkenyl, $C_2$–$C_6$alkynyl, $C_1$–$C_6$alkyl, $C_2$–$C_6$alkenyldialkylmalonyl, $CF_3$, HO—, $C_1$–$C_6$alkyloxy$C_1$–$C_6$alkyloxy, $C_1$–$C_6$alkylSO$_n$ wherein n is 1–2, $C_1$–$C_6$alkylthio, $C_1$–$C_6$alkylacryl, $CF_3O$, $C_1$–$C_4$alkylenedioxy, $C_1$–$C_6$alkylacryl, $R^6R^7N(CO)NR^6$; N-formyl (heterocyclic), $NO_2$, $NR^6R^7C_0$–$C_6$alkyl, wherein $R^6$ and $R^7$ are independently selected from H, $C_1$–$C_6$alkyl, HC(O), $C_1$–$C_6$alkoxy$C_1$–$C_6$alkyl, $C_1$–$C_6$alkoxy, $C_1$–$C_6$alkylC(O), $CF_3C(O)$, $NR^8R^9C_1$–$C_6$alkyl, pthalimido$C_1$–$C_6(O)$, $C_1$–$C_6$alkylSO$_n$ where n is 1–2, $CNC_1$–$C_6$alkyl, $R^8R^9NC(O)R^8$—, heteroaryl, $NR^8R^9C_1$–$C_6$alkylC(O)$,
$C_1$–$C_6$alkoxycarbamido$C_1$–$C_6$alkyl,
wherein $R^8$ and $R^9$ are independently selected from those variables identified for $R^6$ and $R^7$ or $R^6$ and $R^7$ or $R^8$ and $R^9$ may join together with the nitrogen atom to which they are attached to form a 5–7 membered unsubstituted or substituted ring optionally containing 1–3 additional heteroatoms selected from O, N or S wherein the substituents are selected from $C_1$–$C_6$alkyl and wherein, in the case of formula I, a dashed line—indicates a double bond is optionally present.

In a preferred embodiment of the present invention is a compound of Formula (I) or (II) above, wherein $R^5$ is an aryl, arylalkyl, heteroaryl or heterocyclic group or those more particular groups shown above which are within each class.

In a more preferred embodiment of the present invention is a compound of Formula (I) or (II) above, wherein $R^5$ is selected from the group consisting of 4-(dimethylamino)phenyl; 5-dimethylamino-2-pyridinyl; 5-methoxy-2-pyridinyl; 4-methoxyphenyl; 5-methylthiophen-2-yl; 4-(N-methyl-N-(2-methoxyethyl)amino)phenyl; and thiophen-2-yl.

In a preferred embodiment of the present invention is a compound of Formula (I) or (II) above, wherein $R^4$ is an aryl, arylalkyl, heteroaryl or heterocyclic group or those more particular groups shown above which are within each class.

In a more preferred embodiment of the present invention is a compound of Formula (I) or (II) above, wherein $R^4$ is selected from the group consisting of: ethoxycarbonylmethyl; ethyl; 3-fluorophenyl; 3-fluoro-4-methylphenyl; 3,4-dimethoxyphenyl; 3-methoxyphenyl; 4-methoxyphenyl; pentyl; phenyl; 3-(2-propyl)phenyl; and 4-(2-propyl)phenyl.

In another preferred embodiment of the present invention is a compound of Formula (I) or (II) above, wherein $R^3$ is an aryl, arylalkyl, heteroaryl or heterocyclic group or those more particular groups shown above which are within each class.

In another more preferred embodiment of the present invention is a compound of Formula (I) or (II) above, wherein $R^3$ is selected from the group consisting of: 3-bromophenyl; 3-bromo-4-fluorophenyl; 4-bromothiophen-2-yl; 3-chlorophenyl; 3,4-dimethoxyphenyl; 3-fluorophenyl; 3-fluoro-4-methylphenyl; 4-(2-propyl)phenyl; and 3-trifluoromethyl-4-fluorophenyl.

Exemplary and preferred compounds of the invention include:
4-amino-5-(3-bromo-4-fluorophenyl)-6-pentyl-7-(4-(dimethylaminophenyl)pyrido[2,3-d]pyrimidine;
4-amino-5-(3-bromo-4-fluorophenyl)-6-pentyl-7-(thiophen-2-yl)pyrido[2,3-d]pyrimidine;
4-amino-5-(3-bromophenyl)-6-(4-methoxyphenyl)-7-(4-methoxyphenyl)pyrido[2,3-d]pyrimidine;
4-amino-5-(3-bromophenyl)-6-ethyl-7-(thiophen-2-yl)pyrido[2,3-d]pyrimidine;
4-amino-5-(3-bromophenyl)-6-pentyl-7-(thiophen-2-yl)pyrido[2,3-d]pyrimidine;
4-amino-5-(3-bromophenyl)-6-(3,4-dimethoxyphenyl)-7-(thiophen-2-yl)pyrido[2,3-d]pyrimidine;
4-amino-5-(3-bromophenyl)-6-(4-(2-propyl)phenyl)-7-(4-(dimethylamino)phenyl)pyrido[2,3-d]pyrimidine;
4-amino-5-(3-bromophenyl)-6-ethoxycarbonylmethyl-7-(thiophen-2-yl)pyrido[2,3-d]pyrimidine;
4-amino-5-(3-bromophenyl)-6-(3-methoxyphenylmethyl)-7-(thiophen-2-yl)pyrido[2,3-d]pyrimidine;
4-amino-5-(3-bromophenyl)-6-(3,4-dimethoxyphenyl)-7-(4-(dimethylamino)phenyl)pyrido[2,3-d]pyrimidine;
4-amino-5-(4-bromothiophen-2-yl)-6-(3,4-dimethoxyphenyl)-7-(thiophen-2-yl)pyrido[2,3-d]pyrimidine;
4-amino-5-(3-chlorophenyl)-6-(3,4-dimethoxyphenyl)-7-(thiophen-2-yl)pyrido[2,3-d]pyrimidine;
4-amino-5-(3-trifluoromethyl-4-fluorophenyl)-6-(3,4-dimethoxyphenyl)-7-(thiophen-2-yl)pyrido[2,3-d]pyrimidine;
4-amino-5-(3-chlorophenyl)-6-(3,4-dimethoxyphenyl)-7-(4-(dimethylamino)phenyl)pyrido[2,3-d]pyrimidine;
4-amino-5-(3-trifluoromethyl-4-fluorophenyl)-6-(3,4-dimethoxyphenyl)-7-(4-(dimethylamino)phenyl)pyrido[2,3-d]pyrimidine;
4-amino-5-(3-chlorophenyl)-6-(3,4-dimethoxyphenyl)-7-(5-methylthiophen-2-yl)pyrido[2,3-d]pyrimidine;
4-amino-5-(4-bromothiophen-2-yl)-6-(3,4-dimethoxyphenyl)-7-(5-methylthiophen-2-yl)pyrido[2,3-d]pyrimidine;

4-amino-5-(4-bromothiophen-2-yl)-6-(3,4-dimethoxyphenyl)-7-(4-(dimethylamino)phenyl)pyrido[2,3-d]pyrimidine;

4-amino-5-(4-bromothiophen-2-yl)-6-(3,4-dimethoxyphenyl)-7-(4-(N-methyl-N-(2-methoxyethyl)amino)phenyl)pyrido[2,3-d]pyrimidine;

4-amino-5-phenyl-6-(3,4-dimethoxyphenyl)-7-(4-(N-methyl-N-(2-methoxyethyl)amino)phenyl) pyrido[2,3-d]pyrimidine;

4-amino-5-(3-chlorophenyl)-6-(3,4-dimethoxyphenyl)-7-(4-(N-methyl-N-(2-methoxyethyl)amino)phenyl)pyrido[2,3-d]pyrimidine;

4-amino-5-phenyl-6-(3,4-dimethoxyphenyl)-7-(5-methoxy-2-pyridinyl)pyrido[2,3-d]pyrimidine;

4-amino-5-(3-chlorophenyl)-6-(3,4-dimethoxyphenyl)-7-(5-methoxy-2-pyridinyl)pyrido[2,3-d]pyrimidine;

4-amino-5-(3-chlorophenyl)-6-(3,4-dimethoxyphenyl)-7-(5-dimethylamino-2-pyridinyl)pyrido[2,3-d]pyrimidine;

4-amino-5,6-bis(4-(2-propyl)phenyl-7-(4-dimethylaminophenyl)pyrido[2,3-d]pyrimidine;

4-amino-5,6-diphenyl-7-(4-(N-methyl-N-(2-methoxyethyl)amino)phenyl)pyrido[2,3-d]pyrimidine;

4-amino-5,6-diphenyl-7-(4-dimethylaminophenyl)pyrido[2,3-d]pyrimidine;

4-amino-5,6-bis(3-fluorophenyl)-7-(4-dimethylaminophenyl)pyrido[2,3-d]pyrimidine;

4-amino-5,6-bis(3,4-dimethoxyphenyl)-7-(4-dimethylaminophenyl)pyrido[2,3-d]pyrimidine;

4-amino-5,6-bis(3-fluoro-4-methylphenyl)-7-(4-dimethylaminophenyl)pyrido[2,3-d]pyrimidine;

4-amino-5,6-bis(3-fluoro-4-methylphenyl)-7-(thiophen-2-yl)pyrido[2,3-d]pyrimidine;

4-amino-5,6-diphenyl-7-(thiophen-2-yl)pyrido[2,3-d]pyrimidine;

4-amino-5,6-diphenyl-7-(5-dimethylamino-2-pyridinyl)pyrido[2,3-d]pyrimidine;

4-amino-5-phenyl-6-(3,4-dimethoxyphenyl)-7-(5-(dimethylamino)pyridin-2-yl)pyrido[2,3-d]pyrimidine;

4-amino-5-(3-chlorophenyl)-6-(3,4-dimethoxyphenyl)-7-(5-N-(2-methoxyethyl)-N-methylamino)-2-pyridinyl)pyrido[2,3-d]pyrimidine;

4-amino-5-(3-chlorophenyl)-6-phenyl-7-(5-dimethylamino-2-pyridinyl)pyrido[2,3-d]pyrimidine;

4-amino-5-(4-bromothiophen-2-yl)-6-phenyl-7-(5-dimethylamino-2-pyridinyl)pyrido[2,3-d]pyrimidine;

4-amino-5-(3-bromophenyl)-6-phenyl-7-(6-dimethylamino-3-pyridinyl)pyrido[2,3-d]pyrimidine 4-amino-5-(3-bromophenyl)-6-(4-fluorophenyl)-7-(6-morpholinyl-3-pyridinyl)pyrido[2,3-d]pyrimidine;

4-amino-5-phenyl-6-phenyl-7-(6-morpholinyl-3-pyridinyl)pyrido[2,3-d]pyrimidine;

4-amino-5-(3-bromophenyl)-6-phenyl-7-(6-morpholinyl-3-pyridinyl)pyrido[2,3-d]pyrimidine;

4-amino-5-phenyl-6-phenyl-7-(6-(N-methyl-N-(2-methoxyethyl)amino)-3-pyridinyl)pyrido[2,3-d]pyrimidine;

4-amino-5-(4-bromothienyl)-6-phenyl-7-(6-(N-methyl-N-(2-methoxyethyl)amino)-3-pyridinyl)pyrido[2,3-d]pyrimidine;

4-amino-5-(4-bromothienyl)-6-cyclopropyl-7-(6-dimethylamino-3-pyridinyl)pyrido[2,3-]pyrimidine;

4amino-5-(4-bromothienyl)-6-(4-fluorophenyl)-7-(6-morpholinyl-3-pyridinyl)pyrido[2,3-d]pyrimidine;

4amino-5-(3-bromophenyl)-6-phenyl-7-(6-cyclopropylmethylamino-3-pyridinyl)pyrido[2,3-d]pyrimidine;

4-amino-5-phenyl-6-phenyl-7-(6-cyclopropylmethylamino-3-pyridinyl)pyrido[2,3-d]pyrimidine;

4-amino-5-(3-bromophenyl)-6-(4-fluorophenyl)-7-(6-morpholinyl-3-pyridinyl)pyrido[2,3-d]pyrimidine;

4anino-5-(3-chlorophenyl)-6-heptyl-7-(6-morpholinyl-3-pyridinyl)pyrido[2,3-d]pyrimidine;

4-amino-5-phenyl-6-phenylmethyl-7-(6-morpholinyl-3-pyridinyl)pyrido[2,3-d]pyrimidine;

4-amino-5-(4-bromothienyl)-6-heptyl-7-(6-morpholinyl-3-pyridinyl)pyrido[2,3-d]pyrimidine;

4-amino-5-(4-bromothienyl)-6-(1-methylethyl)-7-(6-moipholinyl-3-pyridinyl)pyrido[2,3-d]pyrimidin;

4-amino-5-(4-bromothienyl)-6-phenylmethyl-7-(6-morpholinyl-3-pyridinyl)pyrido[2,3-d]pyrimidine;

4-amino-5-(3-bromophenyl)-6-cyclohexyl-7-(6-dimethylamino-3-pyridinyl)pyrido[2,3-d]pyrimidine; and 4-amino-5-(3-bromophenyl)-6-pentyl-7-(6-dimethylamino-3-pyridinyl)pyrido[2,3-d]pyrimidine and pharmaceutically acceptable salts and amides thereof. The partially saturated and fully saturated versions of the above compounds are also included within the scope of the method of inhibiting adenosine kinase in a patient in need of treatment thereof. The above compounds may be treated with hydrogen and a catalyst to form a compound of formula I wherein the double bonds on the right side are absent or there is a double bond between the 5,6 carbons; the 6,7 carbons or the 7 carbon, 8 nitrogen.

$R^3$, $R^4$ and $R^5$ groups may be independently selected from phenyl; thiophen-2-yl; 1-methyl-2-oxobenzoxazolin-5-yl; 2-(dimethylamino)-5-pyrimidinyl; 2-(N-formyl-N-methyl amino)-3-pyrimidinyl; 2-(N-(2-methoxyethyl)-N-methylamino)-5-pyrimidinyl; 5-dimethylamino-2-pyridinyl; 5-(N-(2-methoxyethyl)-N-methylamino)-2-pyridinyl; 2-(N-methylamino)-5-pyrimidinyl; 2-(1-morpholinyl)-5-pyrimidinyl; 2-(1-pyrrolidinyl)-5-pyrimidinyl; 2-dimethylamino-5-pyrimidinyl; 2-furanyl; 2-oxobenzoxazolin-5-yl; 2-pyridyl; 3-(dimethylamino)phenyl; 3-amino-4-methoxyphenyl; 3-bromo-4-(dimethylamino)phenyl; 3-methoxyphenyl; 3-methyl-4-(N-acetyl-N-methylamino)phenyl; 3-methyl-4-(N-formyl-N-methylamino)phenyl; 3-methyl-4-(N-methyl-N-(trifluoroacetyl)amino)phenyl; 3-methyl-4-(N-methylamino)phenyl; 3-methyl-4-pyrrolidinylphenyl; 3-pyridyl; 3,4-dichlorophenyl; 3,4-methylenedioxyphenyl; 3,4,5-trimethoxyphenyl; 4-(acetylamino)phenyl; 4-(dimethylamino)-3-fluorophenyl; 4-(dimethylamino) phenyl; 4-(imidazol-1-yl)phenyl; 4-(methylthio)phenyl; 4-(morpholinyl)phenyl; 4-(N-(2-(dimethylamino)ethyl)amino)phenyl; 4-(N-(2-methoxyethyl)amino)phenyl; 4-(N-acetyl-N-methylamino)phenyl; 4-(N-ethyl-N-formylamino)phenyl; 4-(N-ethylamino)phenyl; 4-(N-formyl-N-(2-methoxyethyl)amino)phenyl; 4-(N-isopropylamino)phenyl; 4-(N-methyl-N-((2-dimethylamino)ethyl)amino)phenyl; 4-(N-methyl-N-(2-(N-phthalimidyl)acetyl)amino)phenyl; 4-(N-methyl-N-(2-cyano)ethylamino)phenyl; 4-(N-methyl-N-(2-methoxyethyl)amino)phenyl; 4-(N-methyl-N-(3-methoxy)propionylamino)phenyl; 4-(N-methyl-N-acetylamino)phenyl; 4(N-methyl-N-formylamino)phenyl; 4-(N-methyl-N-trifluoroacetylamino)phenyl; 4-(N-morpholinyl)phenyl; 4-(thiophen-2-yl)phenyl; 4-(ureido) phenyl; 4-(2-(dimethylamino)acetylamino)phenyl; 4-(2-(2-methoxy)acetylamino)ethyl)amino)phenyl; 4-(2-methoxy)ethoxyphenyl; 4-(2-oxo-1-oxazolidinyl)phenyl; 4-(4-methoxy-2-butyl)phenyl; 4-(4-methylpiperidinyl)phenyl; 4-(5-pyrimidinyl)phenyl; 4aminophenyl; 4-bromophenyl; 4-butoxyphenyl; 4-carboxamidophenyl; 4-chlorophenyl; 4-cyanophenyl; 4-diethylaminophenyl; 4-diethylmalonylallylphenyl); 4-dimethylaminophenyl; 4-ethoxyphenyl; 4-ethylphenyl; 4-fluorophenyl;

4-hydroxyphenyl; 4-imidazolylphenyl; 4-iodophenyl; 4-isopropylphenyl; 4-methoxyphenyl) 4-methylaminophenyl; 4-methylsulfonylphenyl; 4-morpholinylphenyl; 4-N-(2-(dimethylamino)ethyl)-N-formylamino)phenyl; 4-N-(3-methoxypropionyl)-N-isopropyl-amino)phenyl; 4-N-ethyl-N-(2-methoxyethyl) amino)phenyl; 4-N-formylpiperidinylphenyl; 4-nitrophenyl; 4-piperidinylphenyl; 4-pyridylphenyl; 4-pyrrolidinylphenyl; 4-t-butylacrylphenyl; 5-(dimethylamino)thiophen-2-yl; 5-amino-2-pyridyl; 5-dimethylamino-2-pyrazinyl; 3-dimethylaminopyridazin-6-yl; 5-dimethylamino-2-pyridyl; 5-pyrimidinylphenyl; 6-(N-methyl-N-formylamino)-3-pyridinyl; 6-(N-methyl-N-(2-methoxyethyl)amino)-3-pyridinyl; 6-(2-oxo-oxazolidinyl)-3-pyridinyl; 6-dimethylamino-3-pyridinyl; 6-imidazolyl-3-pyridinyl; 6-morpholinyl-3-pyridinyl; 6-pyrrolidinyl-3-pyridinyl; (2-propyl)-3-pyridinyl; and (4-formylamino) phenyl; (thiophen-2-yl)methyl; (thiophen-3-yl)methyl; butyl; cycloheptyl; pentyl; thiophen-2-yl; 1-(3-bromophenyl)ethyl; 2-(N-phenylmethoxycarbonyl) aminophenyl; 2-(3-bromophenyl)ethyl; 2-(3-cyanophenyl) methyl; 2-(4-bromophenyl)ethyl; 2-(5-chloro-2-(thiophen-3-yl)phenyl; 2-bromophenyl; 2-furanyl; 2-methylpropyl; 2-phenylethyl; phenylmethyl; 2,3-dimethoxyphenyl; 2,3-methylenedioxyphenyl; 3-(furan-2-yl)phenyl; 3-(thiophen-2-yl)phenyl; 3-(2-pyridyl)phenyl; 3-(3-methoxybenzyl) phenyl; 3-(amino)propynyl; 3-benzyloxyphenyl; 3-bromo-4-fluorophenyl; 3-bromo-5-iodophenyl; 3-bromo-5-methoxyphenyl; 3-bromophenyl; 3-bromophenylmethyl; 3-carboxamidophenyl; 3-chlorophenyl; 3-cyanophenyl; 3-diethylmalonylallylphenyl; 3-dimethylaminophenyl; 3-ethoxyphenyl; 3-fluoro-5-trifluoromethylphenyl; 3-fluorophenyl; 3-hydroxyphenyl; 3-iodophenyl; 3-methoxyethyoxyphenyl; 3-methoxyphenyl; 3-methylphenyl; 3-methylsulfonylphenyl; 3-methylthiophenyl; 3-t-butylacrylphenyl; 3-trifloromethyoxyphenyl; 3-trifluoromethylphenyl; 3-vinylpyridinylphenyl; 3,4-dichlorophenyl; 3,4-dimethoxyphenyl; 3,4-methylenedioxyphenyl; 3,4,5-trimethoxyphenyl; 3,5-di(trifluoromethyl)phenyl; 3,5-dibromophenyl; 3,5-dichlorophenyl; 3,5-dimethoxyphenyl; 3,5-dimethylphenyl; 4(2-propyl)phenyl; 4-(2-propyl)oxyphenyl; 4-benzyloxyphenyl; 4-bromophenyl; 4-bromothiophen-2-yl; 4-butoxyphenyl; 4-dimethylaminophenyl; 4-fluoro-3-trifluoromethylphenyl; 4-methoxyphenyl; 4-neopentylphenyl; 4-phenoxyphenyl; 5-bromothiophen-2-yl; cyclohexyl; cyclopropyl; hexyl; methyl; phenyl; (2-bromo-5-chlorophenyl)methyl; (2-bromophenyl)methyl; 6-cyclopropylrnethylamino-3-pyridinyl; and (5-chloro-2-(3-methoxyphenyl)phenyl) methyl.

The term "acyl", as used herein, refers to a moiety attached by a carbonyl linkage, as for example, loweralkyl-carbonyl or aryl-carbonyl, wherein loweralkyl and aryl are as defined herein. Examples of acyl include, for example, acetyl, propionyl, hexanoyl, trifluoroacetyl, benzoyl, 4-methylbenzoyl, methoxyacetyl, pentanoyl, N-Bocglycylimidazoyl, N-phthalimidylglycyl and the like or others as specified herein.

The term "aryl" or "substituted aryl", as used herein, refers to a carbocyclic aromatic radical, including, for example, phenyl and 1- or 2-naphthyl, which may be unsubstituted or substituted respectively by independent replacement of one, two or three of the hydrogen atoms thereon with Cl, Br, F, I, cyano, carboxamido, hydroxy, loweralkoxy, loweralkyl, loweralkenyl, loweralkynyl, amino, loweralkylamino, di(loweralkylamino), N-loweralkyl-N-loweralkoxyamino, trifluoromethyl or methoxymethyl groups. In addition, the term "aryl" refers to a phenyl group substituted with one ureido, methylsulfonyl, pyrimidinyl, pyridinyl, pyridazinyl, morpholinyl, phenyl-loweralkoxy, phenyl-loweralkenyl or cycloalkyl-loweralkyl group. Examples of aryl radicals include, but are not limited to, 3-bromophenyl, 3-chlorophenyl, 4-chlorophenyl, 3-methoxyphenyl, 3-(2-propyl)phenyl, 3,4-dimethoxyphenyl, 3-trifluromethylphenyl, 3-trifluoro-4-fluorophenyl, 4-(N-methyl-N-methoxyl)ethylaminophenyl, 4-dimethylaminophenyl, 3-fluoro-4-methylphenyl, 4-methylphenyl, 4-cyanophenyl, 4-propylmethyl, 3,5-dichlorophenyl, 3,4-methylenedioxyphenyl, 3-cyanopropylphenyl, 4-ureidophenyl, 3-methylsulfonylphenyl, 3-carboxamidopropylphenyl or others as shown herein.

The term "arylalkyl" refers to a loweralkyl radical having appended thereto an aryl group, as defined above, as for example benzyl and phenylethyl.

The term "aryloxy" refers to a aryl radical which is appended to the molecule via an ether linkage (i.e., through an oxygen atom), as for example phenoxy, naphthyloxy, 4-chlorophenoxy, 4methylphenoxy, 3,5-dimethoxyphenoxy, and the like.

The term "cycloalkyl" refers to a cyclic saturated hydrocarbon radical having from 3 to 7 ring atoms. Examples of cycloalkyl include cyclopropyl, cyclobutyl, cyclopentyl, cyclohexyl and cycloheptyl. Cycloalkyl is also described as $C_3$–$C_8$cycloalkyl.

The term "cycloalkyl-loweralkyl" refers to a loweralkyl radical as defined below substituted with a cycloalkyl group as defined above by replacement of one hydrogen atom. Examples of cycloalkyl-loweralkyl include cyclopropylmethyl, cyclobutylethyl, cyclopentylmethyl, cyclohexylmethyl and cycloheptylbutyl, and the like.

The term "heteroaryl" or "substituted heteroaryl" refers to a monocyclic aromatic radical having from five to seven ring atoms of which one ring atom is nitrogen, oxygen or sulfur, zero, one or two ring atoms are additional heteroatoms independently selected from S, O and N; and the remaining ring atoms are carbon, the radical being joined to the rest of the molecule via any of the ring atoms. A heteroaryl group may be unsubstituted or substituted by independent replacement of one, two or three of the hydrogen atoms thereon with Cl, Br, F, I, cyano, carboxamido, hydroxy, loweralkoxy, loweralkyl, loweralkenyl, loweralkynyl, amino, loweralkylamino, di(loweralkylamino), N-loweralkyl-N-loweralkoxyamino, trifluoromethyl or methoxymethyl groups. In addition, the term "heteroaryl " refers to a heteroaryl group substituted with one ureido, methylsulfonyl, pyrimidinyl, pyridinyl, pyridazinyl, morpholinyl, phenyl-loweralkoxy, phenyl-loweralkenyl or cycloalkyl-loweralkyl group. In addition a heteroaryl group may be substituted by replacement of any two adjacent hydrogen atoms with a grouping of atoms to form a fused benzene ring. Examples of heteroaryl include pyridinyl, pyrazinyl, pyrimidinyl, pyrrolyl, pyrazolyl, imidazolyl, thiazolyl, oxazolyl, isoxazolyl, thiadiazolyl, oxadiazolyl, furanyl, thiophenyl, 5-methylthiophen-2-yl, 5-nitrothiophen-2-yl, 5-methylfuranyl, benzofuranyl, benzothiophenyl, and the like and those additionally described herein.

The term "heterocyclic" refers to a saturated or unsaturated monocyclic ring system radical having from four to seven ring atoms of which one is nitrogen or oxygen; zero, one or two ring atoms are additional heteroatoms independently selected from S, O and N; and the remainder are carbon, the radical being joined to the rest of the molecule via any of the ring atoms and being optionally substituted, either on a nitrogen or a carbon atom, by an additional radical selected from among aryl(loweralkyl), alkoxycarbonyl, loweralkyl, halo(loweralkyl), amino (loweralkyl), hydroxy-substituted loweralkyl, hydroxy, loweralkoxy, halogen, amino, loweralkylamino, and amino, (loweralkyl)amino or alkanoylamino of from one to eight carbon atoms in which the amino group may be further substituted with alkanoyl of from one to eight carbons, an alpha-amino acid or a polypeptide. Examples of heterocyclic include pyrrolidine, tetrahydrofuran, dihydropyrrole, isoxazolidine, oxazolidine, tetrahydropyridine, piperidine, piperazine, morpholine, thiomorpholine, aziridine and azetidine and those additionally described herein.

The term "heterocyclic-loweralkyl" refers to a loweralkyl radical as defined below substituted with a heterocyclic-group as defined above by replacement of one hydrogen atom. Examples of cycloalkyl-loweralkyl include pyrrolidinylmethyl, piperidinylethyl, and the like.

The term "loweralkyl", as used herein, refers to saturated, straight- or branched-chain hydrocarbon radicals containing from one to six carbon atoms including, which may be unsubstituted or substituted by independent replacement of one, two or three of the hydrogen atoms thereon with Cl, Br, F, I, cyano, carboxamido, hydroxy, loweralkoxy, amino, loweralkylamino, di(loweralkylamino) or N-loweralkyl-N-loweralkoxyamino groups. Examples of loweralkyl include, but are not limited to, methyl, ethyl, propyl, isopropyl, n-butyl, tert-butyl, neopentyl, n-hexyl, hydroxyethyl, methoxymethyl, trifluoromethyl, 3-cyanopropyl, 3-carboxamidopropyl, and the like. In certain cases, the group "$C_1$–$C_6$alkyl" is described and has a similar meaning as above for loweralkyl but is more specifically recited. Likewise, the term "$C_0$–$C_6$alkyl" indicates the carbon atoms which may be present in the alkyl chain including zero. These terms are also provided adjacent to aryl or heteroaryl or other generic group and represent or have the same meaning as, for example, "arylalkyl" or "heteroarylalkyl".

The term "loweralkenyl", as used herein, refers to mono-unsaturated straight- or branched-chain hydrocarbon radicals containing from two to six carbon atoms including, but not limited to, vinyl, propenyl, n-butenyl, i-butenyl, n-pentenyl, and n-hexenyl. These variables are also recited as, for example, $C_2$–$C_6$alkenyl.

The term "loweralkoxy" refers to a loweralkyl radical which is appended to the molecule via an ether linkage (i.e., through an oxygen atom), as for example methoxy, ethoxy, propoxy, 2-propoxy, 2-methyl-2-propoxy, tert-butoxy, pentyloxy, hexyloxy, isomeric forms thereof and the like. This term is also described as $C_1$–$C_6$alkyloxy.

The term "loweralkynyl", as used herein, refers to straight- or branched-chain hydrocarbon radicals possessing a single triple bond and containing from two to six carbon atoms including, but not limited to, ethynyl, propynyl, n-butynyl, n-pentynyl, and n-hexynyl. This term is also described as $C_2$–$C_6$alkynyl.

The term "mammal" has its ordinary meaning and includes human beings.

In a further aspect of the present invention pharmaceutical compositions are disclosed which comprise a compound of the present invention in combination with a pharmaceutically acceptable carrier.

The present invention includes one or more compounds, as set forth above, formulated into compositions together with one or more non-toxic physiologically tolerable or acceptable diluents, carriers, adjuvants or vehicles that are collectively referred to herein as diluents, for parenteral injection, for oral administration in solid or liquid form, for rectal or topical administration, or the like. As is well known in the art, a compound of the present invention can exist in a variety of forms including pharmaceutically-acceptable salts, amides and the like.

Compositions may be prepared that will deliver the correct amount of a compound or compounds of the invention. The following dosages are thought to provide the optimal therapy: iv infusions: 0.1–250 nmol/kkg/minute, preferably from 1–50 nmol/kg/minute; oral: 0.01–250 μMol/kg/day, preferably from about 0.1–50 μMol/kg/day; these oral molar dosage ranges correspond to 0.005–125 mg/kg/day, preferably 0.05–25 mg/kg/day. For treatment of acute disorders the preferred route of administration is intravenous; the preferred method of treating chronic disorders is orally by means of a tablet or sustained release formulation.

"Pharmaceutically-acceptable amide" refers to the pharmaceutically-acceptable, nontoxic amides of the compounds of the present invention which include amides formed with suitable organic acids or with amino acids, including short peptides consisting of from 1-to-6 amino acids joined by amide linkages which may be branched or linear, wherein the amino acids are selected independently from naturally-occurring amino acids, such as for example, glycine, alanine, leucine, valine, phenylalanine, proline, methionine, tryptophan, asparagine, aspartic acid, glutamic acid, glutamine, serine, threonine, lysine, arginine, tyrosine, histidine, ornithine, and the like.

"Pharmnaceutically-acceptable salts" refers to the pharmaceutically-acceptable, nontoxic, inorganic or organic acid addition salts of the compounds of the present invention, as described in greater detail below.

The compounds of the present invention can be used in the form of pharmaceutically-acceptable salts derived from inorganic or organic acids. These salts include, but are not limited to, the following: acetate, adipate, alginate, aspartate, benzoate, benzenesulfonate, bisulfate, butyrate, camphorate, camphorsulfonate, citrate, cyclopentanepropionate, digluconate, dodecylsulfate, ethanesulfonate, flavianate, fumarate, glucoheptonate, glycerophosphate, hemisulfate, heptonate, hexonoate, hydrochloride, hydrobromide, hydroiodide, 2-hydroxy-ethanesulfonate, lactate, maleate, methanesulfonate, nicotinate, 2-naphthalenesulfonate, oxalate, palmate, pettinate, persulfate, 3-phenylpropionate, phosphate, picrate, pivalate, propionate, succinate, tartrate, thiocyanate, tosylate, and undecanoate.

Appropriate cationic salts are also readily prepared by conventional procedures such as treating an acid of Formula I or II with an appropriate amount of base, such as an alkali or alkaline earth metal hydroxide, e.g., sodium, potassium, lithium, calcium, or magnesium, or an organic base such as an amine, e.g., dibenzylethylenediamine, cyclohexylamine, dicyclohexylamine, triethylamine, piperidine, pyrrolidine, benzylamine, and the like, or a quaternary ammonium hydroxide such as tetramethylammonium hydroxide and the like. Also, the basic nitrogen-containing groups can be quaternized with such agents as loweralkyl halides, such as methyl, ethyl, propyl, and butyl chlorides, bromides, and iodides; dialkyl sulfates; long chain halides such as decyl, lauryl, myristyl, and stearyl chlorides, bromides and iodides; arylalkyl halides like benzyl and phenethyl bromides, and others. Water or oil-soluble or dispersible products are thereby obtained.

The salts of the present invention can be synthesized from the compounds of Formula I or II which contain a basic or acidic moiety by conventional methods, such as by reacting the free base or acid with stoichiometric amounts or with an excess of the desired salt forming inorganic acid or base in a suitable solvent or various combinations of solvents.

Further included within the scope of the present invention are pharmaceutical compositions comprising one or more of the compounds of formula (I) prepared and formulated in combination with one or more non-toxic pharmaceutically acceptable carriers compositions, in the manner described below.

Compositions suitable for parenteral injection may comprise pharmaceutically acceptable sterile aqueous or non-aqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

If desired, and for more effective distribution, the compounds may be incorporated into slow-release or targeted-delivery systems, such as polymer matrices, liposomes, and microspheres. They may be sterilized, for example, by filtration through a bacteria-retaining filter, or by incorporating sterilizing agents in the form of sterile solid compositions, which may be dissolved in sterile water, or some other sterile injectable medium immediately before use.

Solid dosage forms for oral administration may include capsules, tablets, pills, powders, and granules. In such solid dosage forms, the active compound is admixed with at least one inert customary excipient (or carrier), such as sodium citrate or dicalcium phosphate, and additionally (a) fillers or extenders, as for example, starches, lactose, sucrose, glucose, mannitol and silicic acid; (b) binders, as for example, carboxymethylcellulose, alginates, gelatin, polyvinylpyrrolidone, sucrose and acacia; (c) humectants, as for example, glycerol; (d) disintegrating agents, as for example, agar-agar, calcium carbonate, potato or tapioca starch, alginic acid, certain complex silicates and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules, using such excipients as lactose or milk sugar, as well as high molecular weight polyethylene glycols, and the like.

Solid dosage forms such as tablets, dragees, capsules, pills and granules may be prepared with coatings and shells, such as enteric coatings and others well known in this art. They may contain pacifying agents, and may also be of such composition that they release the active compound or compounds in a certain part of the intestinal tract in a delayed manner. Examples of embedding compositions which may be used are polymeric substances and waxes.

The active compounds may also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, these liquid dosage forms may also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal or vaginal administrations are preferably suppositories which can be prepared by mixing the compounds of this invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical or transdermal administration of a compound of this invention further include ointments, pastes, creams, lotions, gels, powders, solutions, sprays, inhalants or transdermal patches. Transdermal administration via a transdermal patch is a particularly effective and preferred dosage form of the present invention. The active component is admixed under sterile conditions with a pharmaceutically acceptable carrier and any needed preservative, buffers or propellants as may be required. It is known that some agents may require special handling in the preparation of transdermal patch formulations. For example, compounds that are volatile in nature may require admixture with special formulating agents or with special packaging materials to assure proper dosage delivery. In addition, compounds which are very rapidly absorbed through the skin may require formulation with absorption-retarding agents or barriers. Ophthalmic formulations, eye ointments, powders and solutions are also contemplated as being within the scope of this invention.

The present compounds may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y., (1976), p 33 et seq.

Synthetic Methods

The compounds and processes of the present invention will be better understood in connection with the following synthetic schemes which illustrate the methods by which the compounds of the invention may be prepared. The $R^1$, $R^2$, $R^3$, $R^4$ and $R^5$ groups are as defined above unless otherwise noted below.

The compounds of the present invention may be synthesized by methods illustrated in Schemes 1–3.

Compound (3) is then reacted with compounds (4, the "$R^5$ reagent") wherein $R^5$ is substituted aryl, heteroaryl, or a heterocyclic compounds to prepare compound (5) according to the literature procedure of Nahm and Weinreb (*Tetrahedron Lett.* 1981, 22: 3815). Compounds (4) are obtainable commercially or easily prepared by standard methods in the art. Compound (5) is then reacted with an appropriately substituted aldehyde (6, the "$R^3$ Reagent"), wherein $R^3$ is aryl, heteroaryl, or a heterocyclic group, and malononitrile (7) by heating in the presence of ammonium acetate, or another suitable ammonium salt, such as for example, ammonium propionate, ammonium iodide, or the like, in an suitable solvent to produce compound (8). Suitable solvents include ethanol, benzene, toluene, methylene chloride, DMF, THF, dioxane, and the like. The water of the reaction may removed by use of a Dean Stork apparatus or by another suitable means, such as 4 Å molecular sieves. The reaction may be performed at from about 40° C. to about

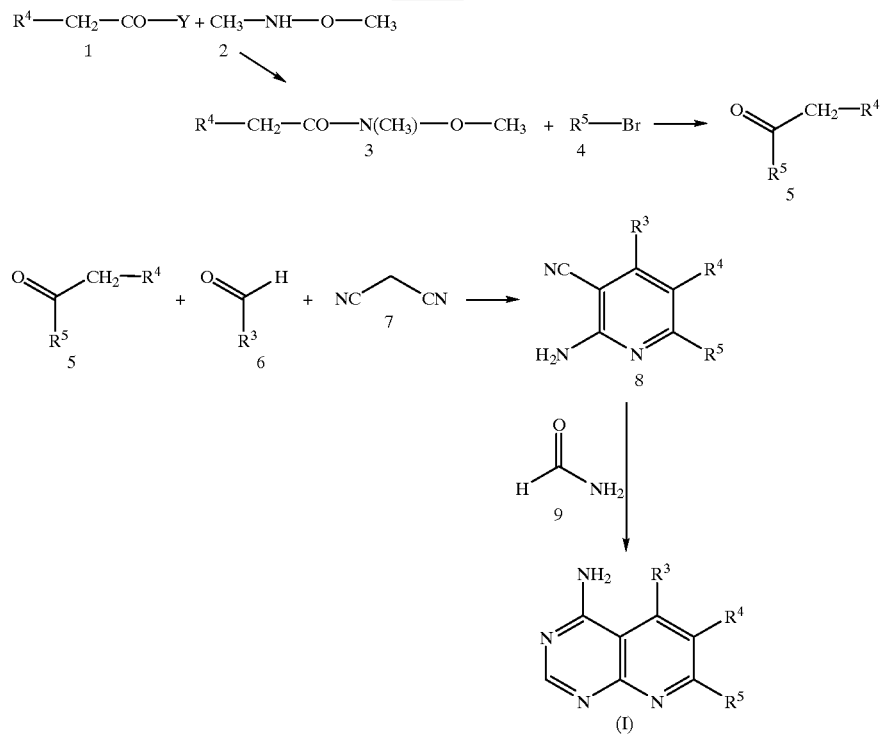

In accordance with Scheme 1, the 5,6,7-trisubstituted compounds wherein $R^5$ and $R^3$ are aryl, heteroaryl, or a heterocyclic group, and $R^4$ is loweralkyl, loweralkenyl, loweralkynyl, aryl, arylalkyl, heteroaryl, or a heterocyclic group are prepared by a modification of a method of Kambe et al., *Synthesis*, 1980, 366–368.

N-methoxy-N-methylamide compounds (3) may be prepared from the appropriate carboxylic acid derivative (1, the "$R^4$ reagent"), wherein Y is OH or Cl, and $R^4$ is loweralkyl, loweralkenyl, loweralkynyl, aryl, arylalkyl, heteroaryl, or a heterocyclic group, by treatment with N,O-dimethylhydroxylamine hydrochloride (2) and 1-(3-dimethylaminopropyl)-3-ethylcarbodiimide (EDCI), t-butanol, and triethylamine. The reaction may be performed in methylene chloride, or a similar suitable solvent, such as for example, toluene or THF, at ambient temperature for about 8 hours to about 24 hours.

200° C., and preferably at the reflux temperature of the solvent, for from about 1 hour to about 24 hours, preferably about 4 hours to 8 hours. The product (8) is preferably purified by chromatography after isolation from the reaction mixture.

The appropriate aldehyde starting materials (6) may be obtained commercially, or may be prepared easily, for example by reductions of esters or acids with DIBAL or another suitable hydride reducing agent, or oxidation of alcohols under Swern conditions, for example. Aliphatic aldehydes do not work effectively by this route. The ketone (5) may, however, include $R^5$ as alkyl groups.

Compound (8) is then treated with excess formamide by heating at reflux. The formation of product is monitored by TLC, and when the reaction is complete (after about 1 to about 8 hours) the reaction mixture is cooled to room temperature. The desired 5,6,7-trisubstituted pyrido[2,3-d]

pyrimidine product (I) is then removed by filtration and purified by column chromatography. This compound may then be partially or fully reduced by catalytic hydrogenation to the partially saturated or fully saturated version(s) (on the right side of the molecule) of the compounds shown in Scheme 1 or of formula I. Stereoisomers produced in the reduction process or step(s) are included within the scope of the invention. The invention also includes those compounds wherein a single bond is between the 5,6 and 7,8 positions and a double bond is present between the 6,7 carbons. The stereoisomers may be isolated and purified by conventional means.

In an alternate procedure, compound (8) is treated by heating with formamidine acetate in ethoxyethanol or diglyme, followed by purification by flash chromatography. In another alternate procedure, compound (8) and ammonium sulfate are heated at reflux in triethyl orthoformate for about 1 to about 8 hours, but preferably about 2 hours. The reaction mixture is cooled and added to a mixture of ammonia in ethanol. The mixture is stirred for about 12 to 24 hours at 25° C., then at reflux for from one to 4 hours, and the solvent is removed in vacuo The residue is purified by trituration with chloroform/ethyl acetate, and the product may be converted to a hydrochloride salt by suspension in 3M HCl, followed by lyophilization.

It is possible to prepare the desired compound of Formula (I) wherein $R^1$ and $R^2$ are not both hydrogen atoms from the compound of Formula (I) wherein $R^1$ and $R^2$ are both hydrogen atoms. When $R^1$ or $R^2$ is loweralkyl this may be accomplished by reaction of the free amino group with the appropriate alkylating reagent, such as an alkyl halide, an alkyl mesylate or an alkyl tosylate, for example, in the presence of a base such as triethylamine or potassium carbonate in a suitable solvent, such as for example, methylene chloride or TBF. When $R^1$ or $R^2$ is arylalkyl this may be accomplished by reaction of the free amino group with the appropriate arylalkyl halide, an alkyl mesylate or an alkyl tosylate, for example, in the presence of a base such as triethylamine or potassium carbonate in a suitable solvent, such as for example, methylene chloride or TBF. When $R^1$ or $R^2$ is acyl this may be accomplished by reaction of the free amino group with the appropriate acid anhydride, acyl chloride or activated acyl group, in the presence of a base such as triethylamine or potassium carbonate in a suitable solvent, such as for example, methylene chloride or THF. When $R^1$ and $R^2$ are taken together with the nitrogen atom to which they are attached to form a 5-to-7 membered ring optionally containing an additional oxygen or nitrogen atom, the compound may be prepared by reacting a precursor compound having a halogen atom in place of the amino group at the 4-position with a 5–7 membered ring compound optionally containing an additional oxygen or nitrogen atom. The precursor compound having a halogen atom in place of the amino group at the 4-position may be prepared by substitution of treatment with sulfuric acid with heating followed by treatment with triethyl orthoformate for the treatment with formamide (cf. Scheme 1 wherein compound (8) is converted to compound (I)) followed by chlorination at the 4-position of the ring by treatment with phosphorous oxychloride or thionyl chloride.

Also, this alternate procedure may be used to prepare alkyl substituted amino compounds, for example by reacting the chloro compound with a mono- or disubstituted amine, such as for example, diethylamine, allyl amine, dibutylamine. This reaction takes place readily in a solvent such as methylene chloride, for example, in the presence of a tertiary amine. Examples of the rings possible wherein $R^1$ and $R^2$ are taken together with the nitrogen atom to which they are attached to form a 5-to-7 membered ring optionally containing an additional oxygen or nitrogen atom, include, but are not limited to, morpholine, piperidine, pyrrolidine, piperazine, thiomorpholine, and the like.

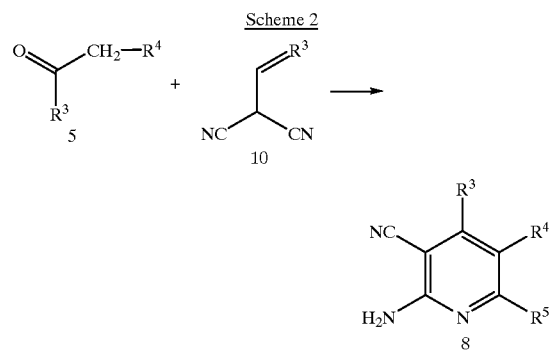

Scheme 2 illustrates an alternate method for preparing the compounds (8) of Scheme 1. Compounds (5), prepared as described above, are reacted with a dicyanoalkene compound (10) by heating at reflux in an alcohol solvent, for example, ethanol or n-butanol to give the compound (8). The dicyano compounds (10) may be prepared from the precursor aldehyde (6) by treatment with malononitrile in 1:1 $H_2O$:EtOH in the presence of a catalytic amount of glycine according to the method of Bastus (*Tetrahedron Lett.*, 1963: 955).

Scheme 3 illustrates an alternate method for preparing compounds of Formula (I) wherein $R^4$ and $R^3$ are the same substitutent A bis-substituted acetylene derivative (11) is treated with catecholborane in THF at reflux for from about 8 to about 48 hours, then 4,6-diamino-5-iodo-pyrimidine (12), saturated aqueous sodium bicarbonate, 3N aqueous sodium hydroxide, and tetrakis(triphenylphosphine) palladium(0) are added. The mixture is then heated at reflux for from about 8 to about 48 hours to give the substituted pyrimidine compound (13). Compound (13) is then treated with the appropriately substituted aldehyde compound (14) to give the desired compound of Formula (I).

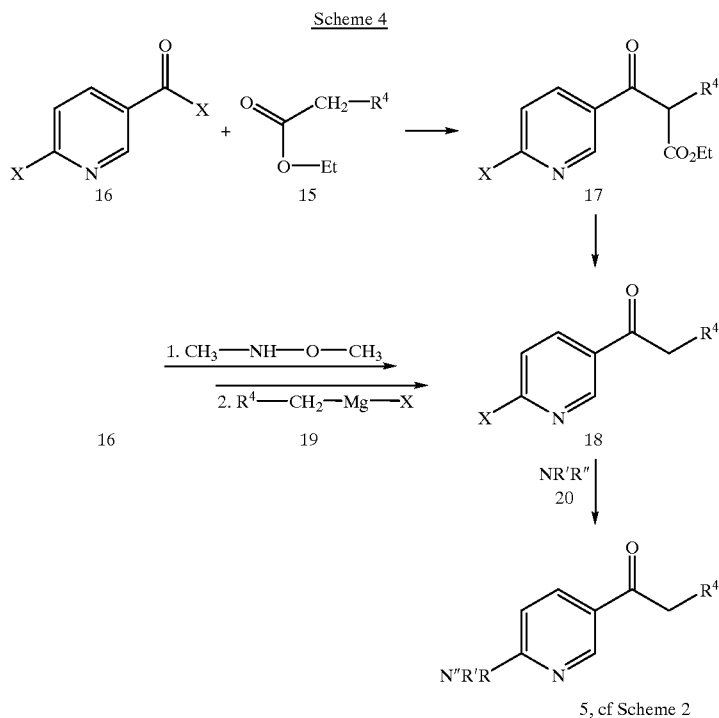

Scheme 4

5, cf Scheme 2

An alternate procedure for preparing compounds of formula (5) is shown in Scheme 4. This procedure is particularly useful when it is desired to have a substituted aryl or heteroaryl moiety in the $R^5$ position.

A compound (15) containing the desired $R^4$ moiety may be reacted with an acyl halide of a halo-substituted compound (16), the ring of which for purposes of illustration only, is shown as a pyridyl ring (eg., 2-halo-5-pyridine carboxylic acid halide), to give the compound (17). Compound (17) in turn is heated to decarboxylate and give compound (18).

Alternately, compound (16) may be treated in a two-step procedure, first with N-methoxymethylamine HCl, then treating the intermediate with compound (19) under Grignard conditions to prepare compound (18).

Compound (18) may then be reacted with an appropriate amine compound (20), where compound (20) may be a heterocyclic compound, such as piperidine, pyrrolidine, or morpholine, for example, or may be a protected or substituted amine, ie. wherein R' and R" are either substituents or amine-protecting groups, or R' and R" are taken together with the N atom which they are attached to form a heterocyclic ring, in order to prepare compound (5).

Method of Inhibiting Kinase

In yet another aspect of the present invention a method of inhibiting adenosine kinase is disclosed. In accordance with that process, an adenosine kinase enzyme is exposed to an effective inhibiting amount of an adenosine kinase inhibitor compound of the present invention. Preferred such compounds for use in the method are the same as set forth above. Means for determining an effective inhibiting amount are well known in the art.

The adenosine kinase to be inhibited can be located in vitro, in situ or in vivo. Where the adenosine kinase is located in vitro, adenosine kinase is contacted with the inhibitor compound, typically by adding the compound to an aqueous solution containing the enzyme, radiolabeled substrate adenosine, magnesium chloride and ATP. The enzyme can exist in intact cells or in isolated subcellular fractions containing the enzyme. The enzyme is then maintained in the presence of the inhibitor for a period of time and under suitable physiological conditions. Means for determining maintenance times are well known in the art and depend inter alia on the concentrations of enzyme and the physiological conditions. Suitable physiological conditions are those necessary to maintain adenosine kinase viability and include temperature, acidity, tonicity and the like. Inhibition of adenosine kinase can be performed, by example, according to standard procedures well known in the art (Yamada, et al., *Comp. Biochem. Physiol.* 1982, 71B: 367–372).

Where the adenosine kinase is located in situ or in vivo, a compound of the invention is typically administered to a fluid perfusing the tissue containing the enzyme. That fluid can be a naturally occuring fluid such as blood or plasma or an artificial fluid such as saline, Ringer's solution and the like. A method of inhibiting adenosine kinase in vivo is particularly useful in mammals such as humans. Administering an inhibitor compound is typically accomplished by the parenteral (e.g., intravenous injection or oral) administration of the compound. The amount administered is an effective inhibiting or therapeutic amount.

By a "therapeutically-effective amount" of the compound of the invention is meant a sufficient amount of the compound to treat or mitigate adenosine kinase related disorders which broadly include those diseases, disorders or conditions which are benefited by inhibition of adenosine kinase, at a reasonable benefit/risk ratio applicable to any medical treatment. It will be understood, however, that the total daily usage of the compounds and compositions of the present invention is to be decided by the attending physician within the scope of sound medical judgment. The specific therapeutically-effective dose level for any particular patient will depend upon a variety of factors including the disorder being treated and the severity of the disorder; activity of the specific compound employed; the specific composition employed; the age, body weight, general health, gender and diet of the patient; the time of administration, route of administration, and rate of excretion of the specific compound employed; the duration of the treatment; drugs used in combination or coincidental with specific compound employed; and the like factors well known in the medical arts and well within the capabilities of attending physicians.

Compounds of the present invention inhibit adenosine kinase activity in vitro and in vivo. In vitro adenosine kinase activity can be measured using any of the standard procedures well known in the art. By way of example, cells containing adenosine kinase, such as IMR-32 human neuroblastoma cells, are cultured in the presence and absence of an inhibitor. Inhibition is measured as the ability to inhibit phosphorylation of endogenous or externally applied $^{14}$C-adenosine by these cells. The cells can be intact or broken. The specificity of adenosine kinase inhibitory activity is determined by studying the effects of inhibitors on adenosine A1 and A2α receptor binding, adenosine deaminase activity and adenosine transport.

Compounds of the present invention are effective in inhibiting adenosine kinase activity in vivo. Numerous animal models for studying adenosine kinase activity and the affects of inhibiting such activity are well known in the art. By way of example, adenosine kinase inhibitors have been reported to protect rodents (e.g., mice and rats) from seizures induced by the subcutaneous administration of pentylenetetrazol (PTZ). Typically the rodents are injected with various doses of a given inhibitor followed at various times by the subcutaneous administration of from about 10 to about 500 milligrams per kilogram of PTZ. The injected animals are then observed for the onset of seizures.

The compounds of the invention were tested in vivo in the hot plate test of analgesia in mammals such as mice. For example, the compounds of examples 19 and 27 in the procedure described directly below were tested thirty minutes after pretreatment with the drugs (30 μmol/kg i.p.) for latency to 10th jump (in seconds). The longer the number of seconds, the more effective the drug at masking the pain felt from the hot plate. Compound 19 resulted in 142.13 seconds relative to the vehicle alone of 72.76±10.51 seconds. Compound 27 resulted in 154.86 seconds. Compounds of the invention are therefore potent pain relievers as demonstrated in this animal model.

Mouse Hot Plate Assay

Male CF1 mice (Charles River) of approximately 25–30 g body weight are pretreated with 10 ml/kg of the test compounds, i.p. or p.o, in groups of 8 animals per dose. At the end of the pretreatment period, the mice are placed in an Omnitech Electronics Automated 16 Animal Hot Plate Analgesia Monitor (Columbus, Ohio; Model AHP16AN) in individual, 9.8×7.2×15.3 cm (l×w×h) plastic enclosures on top of a copper plate warmed to 55° C. Infared sensors located near the top of each enclosure record beam crossings that occur as the mice jump off of the heated surface. Latency times for each jump are automatically recorded, and latency to both the first and tenth jumps are used for data analysis. Mice that do not reach the criteria of 10 jumps by 180 seconds are immediately removed from the hotplate to avoid tissue damage, and they are assigned the maximum value of 180 seconds as their latency to tenth jump.

Numerous other animal models of adenosine kinase activity have been described [See, e.g., Davies, et al., *Biochem. Pharmacol.*, 33:347–355 (1984); Keil, et al., *Eur. J. Pharmacol.*, 271:37–46 (1994); Murray, et al., *Drug Development Res.*, 28:410–415 (1993)].

Numerous inhibitor compounds of the present invention were tested in vitro and found to inhibit adenosine kinase activity. The results of some representative studies are shown in Table 1 below. The data indicate that the compounds inhibit adenosine kinase.

TABLE 1

Inhibition of Adenosine Kinase by Representative Compounds of the Invention

| Compound of Example No. | IC$_{50}$ (nM) |
|---|---|
| 1 | 80 |
| 4 | 3 |
| 6 | 1 |
| 8 | 3 |
| 9 | 23 |
| 11 | 0.3 |
| 12 | 1 |
| 19 | 0.1 |
| 25 | 4 |
| 26 | 5 |
| 27 | 9 |
| 39 | 5 |
| 40 | 3 |
| 41 | 2 |

Method of Treating Cerebral Ischemia, Epilepsy, Nociperception (Nociception) (Pain), Inflammation including conditions such as Septic Shock due to Sepsis Infection In yet another aspect of the present invention a method of treating cerebral ischemia, epilepsy, nociperception or nociception, inflammation including conditions such as septic shock due to sepsis infection in a human or lower mammal is disclosed, comprising administering to the mammal a therapeutically effective amount of a compound.

Alterations in cellular adenosine kinase activity have been observed in certain disorders. Adenosine kinase activity was found to be decreased, relative to normal liver, in a variety of rat hepatomas: activity of the enzyme giving a negative correlation with tumor growth rate (Jackson, et al., *Br. J. Cancer*, 1978, 37: 701–713). Adenosine kinase activity was also diminished in regenerating liver after partial hepatectomy in experimental animals (Jackson, et al., *Br. J. Cancer*, 1978, 37: 701–713). Erythrocyte Adenosine kinase activity was found to be diminished in patients with gout (Nishizawa, et al., *Clin. Chim. Acta* 1976, 67: 15–20). Lymphocyte adenosine kinase activity was decreased in patients infected with the human immunodeficiency virus (HIV) exhibiting symptoms of AIDS, and increased in asymptomatic HIV-seropositive and HIV-seronegative high-risk subjects, compared to normal healthy controls (Renouf, et al., *Clin. Chem.* 1989, 35: 1478–1481). It has been suggested that measurement of adenosine kinase activity may prove useful in monitoring the clinical progress of patients with HBV infection (Renouf, et al., *Clin. Chem.* 1989, 35: 1478–1481). Sepsis infection may lead to a systemic inflammatory syndrome (SIRS), characterized by an increase in cytokine production, neutrophil accumulation, hemodynamic effects, and tissue damage or death. The ability of adenosine kinase inhibitor to elevate adenosine levels in tissues has been demonstrated to ameliorate syndrome symptoms, due to the known anti-inflammatory effects of adenosine. (Firestein, et al., *J. of Immunology*, 1994, pp. 5853–5859). The ability of adenosine kinase inhibitors to elevate adenosine levels is expected to alleviate pain states, since it has been demonstrated that administration of adenosine or its analogs results in antinociception or antinociperception. (Swaynok, et al., *Neuroscience*, 1989, 32: No. 3, pp. 557–569).

The following Examples illustrate preferred embodiments of the present invention and are not limiting of the specification and claims in any way.

EXAMPLE 1

4-amino-5-(3-bromo-4-fluorophenyl)-6-pentyl-7-(4-(dimethylamino)phenyl)pyrido[2,3-d]pyrimidine 4-(3-Bromo-4-fluorophenyl)-3-cyano-6-(dimethylaminophenyl)-5-pentyl-2-pyridineamine (951 mg, 1.98 mmol) was suspended in 2-ethoxyethanol followed by addition of formamidine acetate (411 mg, 3.95 mmol). The reaction was heated to 130° C. for two days during which additional formamidine acetate (2–3 eq. each) was added at several hour intervals. After this time the reaction was cooled, concentrated in vacuo, and the residue was triturated with $CH_2Cl_2$ and filtered. The filtrate was purified by flash chromatography (9% MeOH/$CH_2Cl_2$) which gave a red oil that was triturated with ethyl ether to yield the title compound as a yellow solid (174 mg, 17%). MS 508/510 $(M+H)^+$; IR $(cm^{-1})$ 3480, 2920, 1610, 1550. 820.

The 4-(3-bromo-4-fluorophenyl)-3-cyano-6-(dimethylaminophenyl)-5-pentyl-2-pyridineamine was prepared as follows:

1a. 1-(4-Dimethylaminophenyl)heptan-1-one

Triethylamine (19.6 g, 194 mmol) was added dropwise to a suspension of N,O-dimethylhydroxylamine hydrochloride (6.93 g, 71 mmol) in anhydrous $CH_2Cl_2$ at 0° C. Heptanoylchloride (9.60 g, 65 mmol) was then added dropwise and the reaction was stirred 1 hour. The crude product mixture was poured into water and the separated aqueous phase was extracted with $CH_2Cl_2$. The combined organic layers was washed with aq. HCl, sat. $NaHCO_3$, brine, dried ($Na_2SO_4$), and concentrated in vacuo to give 10 g (89%) N-methyl-N-methoxyheptanamide as a yellow oil.

n-Butyllithium (2.5 M in hexanes, 51 mL, 127 mmol) was added dropwise to 4-bromo-N,N-dimethylaniline (23.1 g, 115 mmol, Aldrich Chemical Co.) in anhydrous THF at −78° C. After 10 min. a solution of N-methyl-N-methoxyheptanamide (10.0 g, 57.7 mmol) in 20 mL THF was added dropwise via canula. The reaction was allowed to proceed 1 hr., then quenched with 1 N aq. HCl and carefully poured into sat. $NaHCO_3$. The aqueous layer was extracted with ethyl ether, and the combined organic fraction was washed with water, brine, dried ($MgSO_4$), and concentrated in vacuo. Flash chromatography (15% EtOAc/hexanes) yielded 1-(4-dimethylaminophenyl)heptan-1-one as a yellow solid (6.49 g, 48%). MS 234 $(M+H)^+$.

1b. 4(3-bromo-4-fluorophenyl)-3-cyano-6-(dimethylaminophenyl)-5-pentyl-2-pyridineamine 1-(4-Dimethylaminophenyl)heptan-1-one (2.15 g, 9.21 mmol), 3-bromo4-fluorobenzaldehyde (1.87 g, 9.21 mmol, the $R^3$ reagent), malononitrile (0.91 g, 13.8 mmol), and $NH_4OAc$ (1.42 g, 18.4 mmol) were dissolved in benzene (75 mL) and heated to reflux. After three days the crude reaction mixture was partitioned between EtOAc and $H_2O$. The organic layer was washed with brine, dried over $Na_2SO_4$, and concentrated in vacuo. The residue was triturated with $Et_2O$, and the resulting solid was collected by filtration yielding 1.25 g of the desired product as a yellow solid (28%): MS 444/446 $(M+H)^+$.

EXAMPLES 2–10

Following the procedures of Example 1, except substituting the appropriate reagents required for $R^5$, $R^4$ and $R^3$ as indicated in Table 2 below, optionally omitting the step of preparing the HCl salt, compounds of Examples 2–10 were prepared as described in Table 3 below.

TABLE 2

Examples 2–10

| Ex. No. | $R^5$ Reagent (for 7-position) | $R^4$ Reagent (for 6-position) | $R^3$ Reagent (for 5-position) |
|---|---|---|---|
| 2 | 2-bromothiophene | heptanoyl chloride | 3-bromo-4-fluorobenzaldehyde |
| 3 | 1-bromo-4-methoxybenzene | 4-methoxyphenylacetyl chloride | 3-bromobenzaldehyde |
| 4 | 2-bromothiophene | butanoyl chloride | 3-bromobenzaldehyde |
| 5 | 2-bromothiophene | heptanoyl chloride | 3-bromobenzaldehyde |
| 6 | 2-bromothiophene | 3,4-dimethoxyphenylacetic acid | 3-bromobenzaldehyde |
| 7 | 1-bromo-4-dimethylamino)benzene | 4-(2-propyl)phenylacetic acid | 3-bromobenzaldehyde |
| 8 | 2-bromothiophene | ethyl succinyl chloride | 3-bromobenzaldehyde |
| 9 | 2-bromothiophene | 3-(3-methoxyphenyl)propionic acid | 3-bromobenzaldehyde |
| 10 | 1-bromo-4-(dimethylamino)benzene | 3,4-dimethoxyphenylacetic acid | 3-bromobenzaldehyde |

TABLE 3

Examples 2–10

| Ex. No. | Name | Analytical Data |
|---|---|---|
| 2 | 4-amino-5-(3-bromo-4-fluorophenyl)-6-pentyl-7-(thiophen-2-yl)pyrido[2,3-d]pyrimidine | IR: 3480, 2920, 1610, 1550, 820; MS m/z 508/510(M + H)⁺. |
| 3 | 4-amino-5-(3-bromophenyl)-6-(4-methoxyphenyl)-7-(4-methoxyphenyl)pyrido[2,3-d]pyrimidine | IR: 3480,3400,3070,1610,1550; MS m/z 513&515 (M + H)⁺. |
| 4 | 4-amino-5-(3-bromophenyl)-6-ethyl-7-(thiophen-2-yl)pyrido[2,3-d]pyrimidine | IR: 3470,3390,3060,1550,1425; MS m/z 411&413 (M + H)⁺. |
| 5 | 4-amino-5-(3-bromophenyl)-6-pentyl-7-(thiophen-2-yl)pyrido[2,3-d]pyrimidine | IR: 3480,3300,3040,1550,1420; MS m/z 453&455 (M + H)⁺. |
| 6 | 4-amino-5-(3-bromophenyl)-6-(3,4-dimethoxyphenyl)-7-(thiophen-2-yl)pyrido[2,3-d]pyrimidine | IR: 3480,3390,3060,1545,1510; MS m/z 519&521 (M + H)⁺. |
| 7 | 4-amino-5-(3-bromophenyl)-6-(4-(2-propyl)phenyl)-7-(4-(dimethylamino)phenyl)pyrido[2,3-d]pyrimidine | IR: 3470,3280,3060,1605,1540; MS m/z 538&540(M + H)⁺. |
| 8 | 4-amino-5-(3-bromophenyl)-6-ethoxycarbonylmethyl-7-(thiophen-2-yl)pyrido[2,3-d]pyrimidine hydrochloride | IR: 3420,3060,1725,1600,1585; MS m/z 469&471(M + H)⁺. |
| 9 | 4-amino-5-(3-bromophenyl)-6-(3-methoxyphenylmethyl)-7-(thiophen-2-yl)pyrido[2,3-d]pyrimidine hydrochloride | IR: 3440,3040,1635,1600,1580; MS m/z 503&505 (M + H)⁺. |
| 10 | 4-amino-5-(3-bromophenyl)-6-(3,4-dimethoxyphenyl)-7-(4-(dimethylamino)phenyl)pyrido[2,3-d]pyrimidine dihydrochloride | IR: 3430,3020,1635,1600,1580; MS m/z 556&558 (M + H)⁺. |

EXAMPLE 11

4-amino-5-(4-bromothiophen-2-y)-6-(3,4-dimethoxyphenyl)-7-(thiophen-2-yl)pyrido[2,3-d] pyrimidine hydrochloride 3-Cyano-4-(4-bromothiophen-2-yl)-5-pentyl-6-(thiophen-2-yl)-2-pyridineamine (750 mg, 1.50 mmol) and formamidine acetate (312 mg, 3.00 mmol) were taken up in 10 mL diglyme and heated to 155° C. Additional formamidine acetate (1 eq) was added at 90 minute intervals over a total of 6 hours, then heating was continued overnight. The cooled reaction mixture was then partitioned between EtOAc and H$_2$O. The organic layer was washed with brine, dried over Na$_2$SO$_4$, and concentrated in vacuo. Flash chromatography (3.5% MeOH/CH$_2$Cl$_2$) gave a brown residue which was dissolved in a small amount of CH$_2$Cl$_2$ followed by addition of Et$_2$O to precipitate the product (209 mg, 26%). This material was converted to the hydrochloride salt using 7M ethanolic HCl followed by precipitation with Et$_2$O and filtration of the product. IR: 525/527; 3420, 2930, 1580, 1510, 820 cm$^{-1}$; MS m/z 498 (M+H)⁺.

The 3-cyano-4-(4-bromothiophen-2-yl)-5-(3,4-dimethoxyphenyl)-6-(thiophen-2-yl)-2-pyridineamine was prepared as follows:

11a. 2-(3,4-dimethoxyphenyl)-1-(thien-2-yl)ethanone (3,4-Dimethoxyphenyl)acetic acid (13.0 g, 66.4 mmol) was suspended in anhydrous CH$_2$Cl$_2$ followed by addition of EDCI (15.3 g, 79.7 mmol), HOBt (20.6 g, 152 mmol), triethylamine (8.06 g, 79.7 mmol), and N,O-dimethylhydroxylamine hydrochloride (6.48 g, 66.4 mmol). The reaction was stirred 3 days at ambient temperature after which the solvent was evaporated at reduced pressure. The residue was partitioned between EtOAc and water. The organic layer was washed with aq. HCl, sat NaHCO$_3$, brine, dried (Na$_2$SO$_4$), and concentrated in vacuo to give 10.5 g (66%) of N-methyl-N-methoxy-(3,4-dimethoxyphenyl) acetamide as a pale brown oil.

2-Lithiothiophene (1.0 M in THF, 33.0 mL, 33.0 mmol, Aldrich Chemical Co.) was added dropwise to N-methyl-N-methoxy-(3,4-dimethoxyphenyl)acetamide (5.26 g, 22.0 mmol) in anhydrous THF at −78° C. The reaction was allowed to proceed 90 min., then diluted with 100 mL Et$_2$O and poured into 1 N aq. HCl. The aqueous phase was extracted with Et$_2$O and the combined organic fraction was washed with brine, dried (Na$_2$SO$_4$), and concentrated in vacuo. Flash chromatography (25% EtOAc/hexanes) yielded 2.91 g (50%) 2-(3,4-dimethoxyphenyl)-1-(thien-2-yl)ethanone as a brown oil. MS 263 (M+H)⁺, 280 (M+NH4)⁺.

11b. 4-bromo-2-(2,2-dicyanoethenyl)thiophene

4-Bromo-2-thiophenecarboxaldehyde (6.92 g, 36.2 mmol) and malononitrile (2.39 g, 36.2 mmol) were dissolved in 100 mL 1:1 EtOH:H2O. A small spatula of glycine was added and the reaction was stirred at ambient temperature for 30 min. The precipitated product was collected by suction filtration, washed with water, and dried under vacuum overnight. The result was 8.38 g (97% ) 4bromo-2-(2,2-dicyanoethenyl)thiophene as a light green solid. MS 238/240 (M+H)+.

11c. 3-cyano-4-(4-bromothiophen-2-yl)-5-(3,4-dimethoxyphenyl)-6-(thiophen-2-yl)-2-pyridineamine 2-(3,4-dimethoxyphenyl)-1-(thien-2-yl)ethanone (1.56 g, 5.95 mmol), 4bromo-2-(2,2-dicyanoethenyl)thiophene (1.71 g, 7.13 mmol), and NH$_4$OAc (1.15 g, 14.9 mmol) were combined in n-BuOH (10 mL) and heated to reflux. After 24 hours. the reaction mixture was cooled, diluted with EtOAc, and washed with water, brine, dried over Na$_2$SO$_4$, and concentrated in vacuo. Flash chromatography (40% EtOAc/hexanes) gave the desired product (0.76 g, 26%) as a dark yellow solid.

EXAMPLES 12–24

Following the procedures of Example 11, except substituting the appropriate reagents required for $R^5$, $R^4$ and $R^3$ as indicated in Table 4 below, compounds of Examples 12–24 were prepared as described in Table 5 below.

TABLE 4

Examples 12–24

| Ex. No. | $R^5$ Reagent (for 7-position) | $R^4$ Reagent (for 6-position) | $R^3$ Reagent (for 5-position) |
|---|---|---|---|
| 12 | 2-bromothiophene | 3,4-dimethoxy-phenylacetic acid | 3-chlorobenzaldehyde |
| 13 | 2-bromothiophene | 3,4-dimethoxy-phenylacetic acid | 3-trifluoromethyl-4-fluorobenzaldehyde |
| 14 | 1-bromo-4-(dimethylamino)benzene | 3,4-dimethoxy-phenylacetic acid | 3-chlorobenzaldehyde |
| 15 | 1-bromo-4-(dimethylamino)benzene | 3,4-dimethoxy-phenylacetic acid | 4-fluoro-3-trifluoromethyl-benzaldehyde |
| 16 | 2-bromo-5-methyl-thiophene | 3,4-dimethoxy-phenylacetic acid | 3-chlorobenzaldehyde |
| 17 | 2-bromo-5-methyl-thiophene | 3,4-dimethoxy-phenylacetic acid | 4-bromo-2-thiophencarboxaldehyde |
| 18 | 1-bromo-4-(dimethylamino)benzene | 3,4-dimethoxy-phenylacetic acid | 4-bromo-2-thiophencarboxaldehyde |
| 19 | 1-bromo-4-(N-methyl-N-(2-methoxyethyl)amino)benzene | 3,4-dimethoxy-phenylacetic acid | 4-bromo-2-thiophencarboxaldehyde |
| 20 | 1-bromo-4-(N-methyl-N-(2-methoxyethyl)amino)benzene | 3,4-dimethoxy-phenylacetic acid | benzaldehyde |
| 21 | 1-bromo-4-(N-methyl-N-(2-methoxyethyl)amino)benzene | 3,4-dimethoxy-phenylacetic acid | 3-chlorobenzaldehyde |
| 22 | 5-bromo-2-methoxypyridine | 3,4-dimethoxy-phenylacetic acid | benzaldehyde |
| 23 | 5-bromo-2-methoxypyridine | 3,4-dimethoxy-phenylacetic acid | 3-chlorobenzaldehyde |
| 24 | 5-bromo-2-dimethylaminopyridine | 3,4-dimethoxy-phenylacetic acid | 3-chlorobenzaldehyde |

TABLE 5

Examples 12–24

| Ex. No. | Name | Analytical Data |
|---|---|---|
| 12 | 4-amino-5-(3-chlorophenyl)-6-(3,4-dimethoxyphenyl)-7-(thiophen-2-yl)pyrido [2,3-d]pyrimidine hydrochloride | IR: 3440, 2940, 1540, 1420, 1020 cm$^{-1}$; MS m/z 475 (M + H)$^+$. |
| 13 | 4-amino-5-(3-trifluoromethyl-4-fluorophenyl)-6-(3,4-dimethoxyphenyl)-7-(thiophen-2-yl)pyrido[2,3-d]pyrimidine hydrochloride | IR: 3460, 3060, 1600, 1510, 1410, 1140; MS m/z 527 (M + H)$^+$. |
| 14 | 4-amino-5-(3-chlorophenyl)-6-(3,4-dimethoxyphenyl)-7-(4-(dimethylamino)phenyl)pyrido[2,3-d]pyrimidine dihydrochloride | IR: 3440, 2940, 1600, 1570, 1360, 1170; MS m/z 512 (M + H)$^+$. |
| 15 | 4-amino-5-(3-trifluoromethyl-4-fluorophenyl)-6-(3,4-dimethoxyphenyl)-7-(4-(dimethylamino)phenyl)pyrido[2,3-d]pyrimidine dihydrochloride | IR: 3450, 3020, 1605, 1510, 1320, 1140; MS m/z 564 (M + H)$^+$. |
| 16 | 4-amino-5-(3-chlorophenyl)-6-(3,4-dimethoxyphenyl)-7-(5-methylthiophen-2-yl)pyrido [2,3-d]pyrimidine hydrochloride | IR: 3440, 2920, 1600, 1570, 1440, 1360; MS m/z 489 (M + H)$^+$. |
| 17 | 4-amino-5-(4-bromothiophen-2-yl)-6-(3,4-dimethoxyphenyl)-7-(5-methylthiophen-2-yl)pyrido [2,3-d]pyrimidine hydrochloride | IR: 3420, 2960, 1580, 1440, 820; MS m/z 539/541(M + H)$^+$. |
| 18 | 4-amino-5-(4-bromothiophen-2-yl)-6-(3,4-dimethoxyphenyl)-7-(4-(dimethylamino)phenyl)pyrido [2,3-d]pyrimidine dihydrochloride | IR: 3420, 2920, 1600, 1380, 820; MS m/z 562/564 (M + H)$^+$. |

TABLE 5-continued

Examples 12–24

| Ex. No. | Name | Analytical Data |
|---|---|---|
| 19 | 4-amino-5-(4-bromothiophen-2-yl)-6-(3,4-dimethoxyphenyl)-7-(4-(N-methyl-N-(2-methoxyethyl)amino)phenyl)pyrido [2,3-d]pyrimidine hydrochloride | IR: 3420, 2920, 1600, 1380, 820; MS m/z 606/608(M + H)$^+$. |
| 20 | 4-amino-5-phenyl-6-(3,4-dimethoxyphenyl)-7-(4-(N-methyl-N-(2-methoxyethyl)amino)phenyl)-5-phenylpyrido [2,3-d]pyrimidine hydrochloride | IR: 3420, 2930, 1630, 1600, 1570, 1360; MS m/z 522 (M + H)$^+$. |
| 21 | 4-amino-5-(3-chlorophenyl)-6-(3,4-dimethoxyphenyl)-7-(4-(N-methyl-N-(2-methoxyethyl)amino)phenyl)pyrido [2,3-d]pyrimidine hydrochloride | IR: 3440, 2930, 1605, 1570, 1355, 1025; Ms m/z 556 (M + H)$^+$. |
| 22 | 4-amino-5-phenyl-6-(3,4-dimethoxyphenyl)-7-(5-methoxy-2-pyridinyl)pyrido [2,3-d]pyrimidine hydrochloride | IR: 3420, 3000, 1600, 1320, 1030; MS m/z 466 (M + H)$^+$. |
| 23 | 4-amino-5-(3-chlorophenyl)-6-(3,4-dimethoxyphenyl)-7-(5-methoxy-2-pyridinyl)pyrido [2,3-d]pyrimidine hydrochloride | IR: 3440, 3000, 1635, 1600, 1365; MS m/z 500 (M + H)$^+$. |
| 24 | 4-amino-5-(3-chlorophenyl)-6-(3,4-dimethoxyphenyl)-7-(5-dimethylamino-2-pyridinyl)pyrido [2,-3-d]pyrimidine dihydrochloride | IR: 3435, 2950, 1645, 1600, 1260; MS m/z 513 (M + H)$^+$. |

EXAMPLE 25

4-amino-5,6-(bis-4-(2-propyl)phenyl)-7-(4-dimethylaminophenyl)pyrido[2.3-d]pyrimidine A sample of 4,6-diamino-5-(1,2-bis(4-(2-propyl)phenyl) ethenyl)pyrimidine (745 mg, 2 mmol) was dissolved in 20 mL 1,2,4-trichlorobenzene containing 4-dimethylaininobenzaidehyde (0.89 g, 6 mmol), and approximately 1 g of 4 Å molecular sieves were added to the reaction mixture. The mixture was heated to reflux for 20 hours, cooled, and filtered through a pad of celite. The filtrate was applied directly to a silica gel chromatography column, which was eluted with 2.5% (19:1 ethanol:amnmonium hydroxide) in ethyl acetate to give the desired product (186 mg, 18.5% yield): IR 3460, 2960, 1605, 1555, 1540, 1525, 1350, 820; MS m/z 502 (M+H)$^+$.

The 4,6-diamino-5-(1,2-bis(4-isopropylphenyl)ethenyl) pyrimidine was prepared as follows:

25a. 1,2-Bis(4-(2-propyl)phenyl)acetylene

To a solution of 4-iodoisopropylbenzene (12.3 g, 50 mmol, Lancaster Chemical Co.) in triethylamine (150 mL) was added trimethylsilylacetylene (5.89 g, 60 mmol), dichlorobis(triphenylphosphine)palladium(II) (0.70 g, 1 mmol, Aldrich), and copper(I) iodide (1.5 g). The reaction was stirred at room temperature for 18 hours, diluted with hexanes and filtered. The filtrate was evaporated under reduced pressure to give crude 1-(4-(2-propyl)phenyl)-2-trimethylsilyl acetylene.

The crude 1-(4-(2-propyl)phenyl)-2-trimethylsilylacetylene was dissolved in methanol (100 mL). Aqueous 1M potassium carbonate solution (25 mL) was added and the reaction stirred at room temperature for 2 hours. The reaction mixture was then diluted with water and extracted with pentane. The organic layers were combined, dried with magnesium sulfate, and evaporated under reduced pressure without heating to give crude 4-(2-propyl) phenylacetylene.

The crude 4-isopropylphenylacetylene was dissolved in triethylamine (100 mL). 4-iodoisopropylbenzene (12.3 g, 50 mmol), dichlorobis(triphenylphosphine)palladium(II) (0.70 g, 1 mmol), and copper(I) iodide (1.5 g) were added. The reaction was stirred at room temperature for 2 days, heated to reflux for 1 hour, cooled, diluted with hexanes, and filtered. The filtrate was evaporated under reduced pressure. The residue was filtered through a pad of silica gel with hexanes, and the solvent was evaporated to give 11.40 g (87%) of 1,2-bis(4-(2-propyl)phenyl)acetylene.

25b. 4,6-diamino-5-(1,2-bis(4-isopropylphenyl)ethenyl) pyrimidine 1,2-Bis(4-(2-propyl)phenyl)acetylene (11.40 g, 43 mmol) was dissolved in 50 mL THF, catecholborane (1 M, 50 mL) in THF was added, and the mixture was heated at reflux for 30 hours. The mixture was cooled, then 4,6-diamino-5-iodo-pyrimidine, 30 mL saturated aqueous sodium bicarbonate, 20 mL 3N aqueous sodium hydroxide, and 1.00 g (0.87 mmol) tetrakis(triphenylphosphine)palladium(0) were added. The mixture was heated to reflux for 18 hours, cooled, diluted with water, then extracted with ethyl acetate. The organic layers were combined, dried with magnesium sulfate, and the solvent evaporated. The residue was chromatographed on silica gel with 2.5% to 5% (19:1 ethanol:ammonium hydroxide) in ethyl acetate to give the desired product (4.53 g, 28% yield).

EXAMPLES 26–32

Following the procedures of Example 25, except substituting the appropriate reagents required for $R^5$, $R^4$ and $R^3$ as indicated in Table 6 below, compounds of Examples 26–32 were prepared as described in Table 7 below.

TABLE 6

Examples 26–32

| Ex. No. | R⁵ Reagent (for 7-position) | R⁴-R³ Reagent (for 5 and 6-positions) |
|---|---|---|
| 26 | 4-(N-(2-methoxyethyl)-N-methylamino)benzaldehyde | 1,2-diphenylacetylene |
| 27 | 4-dimethylamino-benzaldehyde | 1,2-diphenylacetylene |
| 28 | 4-dimethylamino-benzaldehyde | 1,2-bis(3-fluorophenyl)acetylene |
| 29 | 4-dimethylamino-benzaldehyde | 1,2-bis(3,4-dimethoxyphenyl)acetylene |
| 30 | 4-dimethylamino-benzaldehyde | 1,2-bis(3-fluoro-4-methylphenyl)acetylene |
| 31 | thiophen-2-carboxaldehyde | 1,2-bis(3-fluoro-4-methylphenyl)acetylene |
| 32 | thiophen-2-carboxaldehyde | 1,2-diphenylacetylene |

TABLE 7

Examples 27–32

| Ex. No. | Name | Analytical Data |
|---|---|---|
| 26 | 4-amino-5-phenyl-6-phenyl-7-(4-(N-methyl-N-(2-methoxyethyl)amino)phenyl)pyrido[2,3-d]pyrimidine hydrochloride | IR: 3420, 3020, 1600, 1580, 1365; MS m/z 462 (M + H)⁺. |
| 27 | 4-amino-5,6-diphenyl-7-(4-dimethylaminophenyl)pyrido[2,3-d]pyrimidine dihydrochloride | IR: 3410, 1635, 1600, 1580, 1360, 705 cm⁻¹; Ms m/z 418 (M + H)⁺. |
| 28 | 4-amino-5,6-bis(3-fluorophenyl)-7-(4-dimethylaminophenyl)pyrido[2,3-d]pyrimidine | IR: 3450, 3060, 1605, 1540, 1345, 1200 cm⁻¹; MS m/z 454 (M + H)⁺. |
| 29 | 4-amino-5,6-bis(3,4-dimethoxyphenyl)-7-(4-dimethylaminophenyl)pyrido[2,3-d]pyrimidine trihydrochloride | IR: 3400, 3100–2800, 1630, 1600, 1575, 1510, 1360, 1250, 1140, 1020 cm⁻¹; MS m/z 538 (M + H)⁺. |
| 30 | 4-amino-5,6-bis(3-fluoro-4-methylphenyl)-7-(4-dimethylaminophenyl)pyrido[2,3-d]pyrimidine dihydrochloride | IR: 3330, 3100–2800, 1635, 1600, 1575, 1535, 1505, 1360, 1200 cm⁻¹; MS m/z 482 (M + H)⁺. |
| 31 | 4-amino-5,6-bis(3-fluoro-4-methylphenyl)-7-(thiophen-2-yl)pyrido[2,3-d]pyrimidine hydrochloride | IR: 3330, 3100–2800, 1635, 1580, 1540, 1505, 1415, 1365, 1235 cm⁻¹; MS m/z 445 (M + H)⁺. |
| 32 | 4-amino-5,6-diphenyl-7-(thiophen-2-yl)pyrido[2,3-d]pyrimidine | IR: 3470, 3390, 3050, 1540, 1420 cm⁻¹ |

TABLE 8

Examples 33–38

| Ex. No. | R⁵ Reagent (for 7-position) | R⁴ Reagent for 6-position | R³ Reagent (for 5-position) |
|---|---|---|---|
| 33 | 5-bromo-2-(dimethylamino)pyridine | phenylacetic acid | benzaldehyde |
| 34 | 5-bromo-2-(dimethylamino)pyridine | 3,4-dimethoxy-phenylacetic acid | benzaldehyde |
| 35 | 5-bromo-2-(N-methyl-N-(methoxyethyl)amino)-pyridine | 3,4-dimethoxy-phenylacetic acid | 3-chlorobenzaldehyde |
| 36 | 5-bromo-2-(dimethylamino)pyridine | phenylacetic acid | 3-chlorobenzaldehyde |
| 37 | 5-bromo-2-(dimethylamino)pyridine | phenylacetic acid | 4-bromothiophen-2-carboxaldehyde |
| 38 | 5-bromo-2-(dimethylamino)pyridine | phenylacetic acid | 3-bromobenzaldehyde |

TABLE 9

Examples 33–38

| Ex. No. | Name | Analytical Data |
|---|---|---|
| 33 | 4-amino-5,6-diphenyl-7-(5-dimethylamino-2-pyridinyl)pyrido [2,3-d]pyrimidine hydrochloride | IR: 3400, 3040, 1640, 1565, 1365 cm$^{-1}$; MS m/z 419 (M + H)$^+$. |
| 34 | 4-amino-5-phenyl-6-(3,4-dimethoxyphenyl)-7-(5-(dimethylamino)pyridin-2-yl)pyrido [2,3-d]pyrimidine hydrochloride | IR: 3420, 2930, 1645, 1600, 1255; MS m/z 479 (M + H)$^+$. |
| 35 | 4-amino-5-(3-chlorophenyl)-6-(3,4-dimethoxyphenyl)-7-(5-(N-(2-methoxyethyl)-N-methylamino)-2-pyridinyl)pyrido [2,3-d]pyrimidine dihydrochloride | IR: 3040, 2930, 1640, 1600, 1370; MS m/z 557 (M + H)$^+$. |
| 36 | 4-amino-5-(3-chlorophenyl)-6-phenyl-7-(5-dimethylamino-2-pyridinyl)pyrido [2,3-d]pyrimidine dihydrochloride | IR: 3420, 3040, 1650, 1575, 1260; MS m/z 453 (M + H)$^+$. |
| 37 | 4-amino-5-(4-bromothiophen-2-yl)-6-phenyl-7-(5-dimethylamino-2-pyridinyl)pyrido [2,3-d]pyrimidine hydrochloride | IR: 3400, 3100, 1650, 1355; MS m/z 503/505 (M + H)$^+$. |
| 38 | 4-amino-5-(3-bromophenyl)-6-phenyl-7-(5-dimethylamino-2-pyridinyl)pyrido [2,3-d]pyrimidine hydrochloride | IR: 3450, 3050, 1650, 1575; MS m/z 497/499 (M + H)$^+$. |

EXAMPLE 39

4-amino-5-(3-bromophenyl)-6-(4-fluorophenyl)-7-(6-morpholinyl-3-pyridinyl)pyrido[2,3-d]pyrimidine hydrochloride Step 39a.1-(6-chloro-3-pyridyl)-2-(4-fluorophenyl)ethanone A solution of ethyl (p-fluorophenyl)acetate (12.1 g, 68.8 mmol, the R$^4$ reagent) in 10 mL THF was added dropwise to a solution of lithium bis(trimethylsilyl)amide (138 mmol) in 150 mL THF at −78° C. The reaction was stirred for 60 min followed by addition of 6-chloronicotinyl chloride (solid, the R$^5$ reagent) in one portion. The reaction was stirred an additional 60 min, then quenched with saturated ammonium chloride solution. The mixture was diluted with Et$_2$O, poured into water, and the aqueous phase was extracted with Et2O. The combined organic layers were washed with brine, dried (Na$_2$SO$_4$), and concentrated in vacuo to 27.1 g crude product as a yellow solid. This material was dissolved in DMSO (200 mL) and H$_2$O (10 mL), and the solution was heated to 155° C. for 3 hours. The reaction was then cooled, poured into water, and the product was extracted with Et$_2$O. The combined Et$_2$O layers were washed with water, brine, dried (MgSO$_4$), and concentrated under vacuum. The product was purified by flash chromatography eluting with 30% EtOAc/hexanes which gave 3.02 g (19%) of the title compound as a yellow solid: MS 250 (M+H)$^+$.

Step 39b. 2-(4-fluorophenyl)-1-(2-morpholinyl-5-pyridyl)ethanone

The ketone compound from Step 39a (3.02 g, 12.1 mmol) and morpholine (4.30 mL, 48.4 mmol) were dissolved in 30 mL absolute ethanol, and the mixture was heated to reflux for 18 hours. The volatiles were then removed under vacuum, and the residue was partitioned between Et$_2$O and saturated NaHCO$_3$. The Et$_2$O layer was washed with brine, dried (Na$_2$SO$_4$), and concentrated under vacuum to give the title compound (3.42 g, 94%) as a yellow solid. MS: 301 (M+H)$^+$.

Step 39c. 4-amino-5-(3-bromophenyl)-6-(4-fluorophenyl)-7-(6-morpholinyl-3-pyridinyl)pyrido[2,3-d]pyrimidine hydrochloride Following the procedure of Example 11 Step C, except substituting the compound from Step 39b for the compound of Example 11 Step a, and substituting 3-bromobenzaldehyde for the 4-bromo-2-thiophenecarboxaldehyde of Example 11b, then carrying the reaction product forward as in Example 1, the title compound was prepared MS m/z (M+H)$^+$ 557; IR (cm$^{-1}$)3433, 3040, 1641, 1602, 1367.

EXAMPLES 40–47

Following the procedures of Example 39 and Example 11, except substituting the reagents shown below for the R$^3$ and R$^4$ reagents and the reagent shown for the 7-position moiety for the morpholine of Example 39 Step b, the compounds shown in Table 10 below were prepared.

TABLE 10

Examples 40–47

| Ex. No. | 5-position | 6-position | Step 39b reagent/ 7-position moiety |
|---|---|---|---|
| 40 | benzaldehyde | ethyl phenylacetate | morpholine/ 6-morpholinyl-3-pyridine |
| 41 | 3-bromobenzaldehyde | ethyl phenylacetate | morpholine/ 6-morpholinyl-3-pyridine |

TABLE 10-continued

| | | | |
|---|---|---|---|
| 42 | benzaldehyde | ethyl phenylacetate | N-methyl-N-(2-methoxyethyl)amine/ 6-(N-methyl-N-(2-methoxyethyl)amino)-3-pyridine |
| 43 | 4-bromo-2-thiophenecarboxaldehyde | ethyl phenylacetate | N-methyl-N-(2-methoxyethyl)amine/ 6-(N-methyl-N-(2-methoxyethyl)amino-3-pyridine |
| 44 | 4-bromo-2-thiophenecarboxaldehyde | ethyl 2-cyclopropylacetate | dimethylamine/ 6-dimethylamino-3-pyridine |
| 45 | 4-bromo-2-thiophenecarboxaldehyde | ethyl (4-fluorophenyl)acetate | morpholine/ 6-morpholinyl-3-pyridine |
| 46 | 3-bromobenzaldehyde | ethyl phenylacetate | cyclopropylmethylamine/ 6-cyclopropylmethylamino-3-pyridine |
| 47 | benzaldehyde | ethyl phenylacetate | cyclopropylmethylamine/ 6-cyclopropylmethylamino-3-pyridine |

Analytical Data, Examples 40–47

| Ex. No. | Name | Analytical data |
|---|---|---|
| 40 | 4-amino-5-phenyl-6-phenyl-7-(6-morpholinyl-3-pyridinyl)pyrido [2,3-d]pyrimidine hydrochloride | MS m/z (M + H)$^+$ 461; IR (cm$^{-1}$) 3431, 3050, 1600, 1576, 1245. |
| 41 | 4-amino-5-(3-bromophenyl)-6-phenyl-7-(6-morpholinyl-3-pyridinyl)pyrido [2,3-d]pyrimidine hydrochloride | MS m/z (M + H)$^+$ 539; IR (cm$^{-1}$) 3423, 2855, 1639, 1600, 1367 |
| 42 | 4-amino-5-phenyl-6-phenyl-7-(6-(N-methyl-N-(2-methoxyethyl)amino)-3-pyridinyl)pyrido [2,3-d]pyrimidine hydrochloride | MS m/z (M + H)$^+$ 463; IR (cm$^{-1}$) 3419, 2932, 1644, 1580, 1367 |
| 43 | 4-amino-5-(4-bromothienyl)-6-phenyl-7-(6-(N-methyl-N-(2-methoxyethyl)amino)-3-pyridinyl)pyrido [2,3-d]pyrimidine hydrochloride | MS m/z (M + H)$^+$ 547; IR (cm$^{-1}$) 3417, 3053, 2928, 1643, 1367 |
| 44 | 4-amino-5-(4-bromothienyl)-6-cyclopropyl-7-(6-dimethylamino-3-pyridinyl)pyrido [2,3-d]pyrimidine hydrochloride | MS m/z (M + H)$^+$ 467; IR (cm$^{-1}$) 3426, 3001, 1649, 1600, 1373 |
| 45 | 4-amino-5-(4-bromothienyl)-6-(4-fluorophenyl)-7-(6-moropholinyl-3-pyridinyl)pyrido [2,3-d]pyrimidine hydrochloride | MS m/z (M + H)$^+$ 563; IR (cm$^{-1}$) 3417, 2969, 1602, 1571, 1367 |
| 46 | 4-amino-5-(3-bromophenyl)-6-phenyl-7-(6-cyclopropylmethylamino-3-pyridinyl)pyrido [2,3-d]pyrimidine hydrochloride | MS m/z (M + H)$^+$ 523; IR (cm$^{-1}$) 3430, 3000, 1650, 1630, 1600 |
| 47 | 4-amino-5-phenyl-6-phenyl-7-(6-cyclopropylmethylamino-3-pyridinyl)pyrido [2,3-d]pyrimidine hydrochloride. | MS m/z (M + H)$^+$ 445; IR (cm$^{-1}$) 3410, 3900, 1655, 1600, 1375 |

EXAMPLE 48

252029.3

4-amino-5-(3-bromophenyl)-6-phenylmethyl-7-(6-morpholinyl-3-pyridinyl)pyrido[2,3-d]pyrimidine hydrochloride Step 48a. 1-(6-chloro-3-pyridyl)-3-phenylpropanone A sample of 6-chloronicotinyl chloride (15.4 g, 87.4 mmol) was added to a mixture of N,O-dimethylhydroxylamine hydrochloride (9.38 g, 96.2 mmol) and triethylaniine (36.6 mL, 262 mmol) in 200 mL CH$_2$Cl$_2$ cooled to 0° C. The reaction was stirred for 2 hours, poured into water. The separated organic layer was washed with brine, dried (Na$_2$SO$_4$) and concentrated under vacuum to give 14.6 g of the intermediate Weinreb amide as a light brown oil. A sample of the intermediate amide (4.09 g, 20.4 mmol) in 100 mL THF was cooled to −78° C. followed by addition of phenethylmragnesium chloride (30.6 mL, 30.6 mmol, 1 M in THF). The reaction was allowed to warm to ambient temperature and stir 3 hours after which it was quenched by 1N aq HCl. The mixture was partitioned between Et$_2$O and saturated NaHCO$_3$. The organic layer was washed with brine, dried (Na$_2$SO$_4$), and concentrated in vacuo. The crude product was purified by flash chromatography eluting with 30% EtOAc/hexanes which gave 3.77 g (75%) of the desired product as a white solid. MS: 246 (M+H)$^+$.

Step 48b. 1-(6-morpholinyl-3-pyridyl)-3-phenylpropanone

Following the procedure of Example 39b, the compound from Step 48a was converted into the title compound.

Step 48c. 4amino-5-(3-bromophenyl)-6-phenylmethyl-7-(6-morpholinyl-3-pyridinyl)pyrido[2,3-d]pyrimidine hydrochloride Following the procedure of Example 11 Step c, except substituting the compound from Step 48b for the compound of Example 11 Step a, and substituting 3-bromobenzaldehyde for the 4-bromo-2-thiophenecarboxaldehyde of Example 11b, then carrying the reaction product forward as in Example 11, the title compound was prepared MS m/z (M+H)+ 553; IR (cm−1) 3430, 3050, 1640, 1600, 1360.

EXAMPLES 49–55

Following the procedures of Example 48 and Example 11, except substituting the reagents shown below for the $R^3$ and $R^4$ reagents and the reagent shown for the 7-position moiety for the morpholine of Example 48 Step b, the compounds shown in Table 11 below were prepared.

TABLE 11

Examples 49–55

| Ex. No. | 5-position | 6-position | Step 48b reagent/ 7-position moiety |
|---|---|---|---|
| 49 | 3-chlorobenzaldehyde | n-octyl magnesium chloride | morpholine/ 6-morpholinyl-3-pyridine |
| 50 | benzaldehyde | phenethyl magnesium chloride | morpholine/ 6-morpholinyl-3-pyridine |
| 51 | 4-bromo-2-thiophenecarboxaldehyde | n-octyl magnesium chloride | morpholine/ 6-morpholinyl-3-pyridine |
| 52 | 4-bromo-2-thiophenecarboxaldehyde | isobutyl magnesium chloride | morpholine/ 6-morpholinyl-3-pyridine |
| 53 | 4-bromo-2-thiophenecarboxaldehyde | phenethyl magnesium chloride | morpholine/ 6-morpholinyl-3-pyridine |
| 54 | 3-bromobenzaldehyde | cyclohexylmethyl magnesium chloride | dimethylamine/ 6-dimethylamino-3-pyridine |
| 55 | 3-bromobenzaldehyde | n-hexyl magnesium chloride | dimethylamine/ 6-dimethylamino-3-pyridine |

Analytical Data, Examples 49–55

| Ex. No. | Name | Analytical data |
|---|---|---|
| 49 | 4-amino-5-(3-chlorophenyl)-6-heptyl-7-(6-morpholinyl-3-pyridinyl)pyrido [2,3-d]pyrimidine hydrochloride | MS m/z (M + H)+ 517; IR (cm−1) 3430, 2940, 1650, 1600, 1380 |
| 50 | 4-amino-5-phenyl-6-phenylmethyl-7-(6-morpholinyl-3-pyridinyl)pyrido [2,3-d]pyrimidine hydrochloride | MS m/z (M + H)+ 475; IR (cm−1) 3430, 2850, 1640, 1600, 1385 |
| 51 | 4-amino-5-(4-bromothienyl)-6-heptyl-7-(6-morpholinyl-3-pyridinyl)pyrido [2,3-d]pyrimidine hydrochloride | MS m/z (M + H)+ 567; IR (cm−1) 3420, 2940, 1625, 1600, 1380 |
| 52 | 4-amino-5-(4-bromothienyl)-6-(1-methylethyl)-7-(6-morpholinyl-3-pyridinyl)pyrido [2,3-d]pyrimidine hydrochloride | MS m/z (M + H)+ 511; IR (cm−1) 3410, 3000, 1650, 1600, 1250 |
| 53 | 4-amino-5-(4-bromothienyl)-6-phenylmethyl-7-(6-morpholinyl-3-pyridinyl)pyrido [2,3-d]pyrimidine hydrochloride | MS m/z (M + H)+ 559; IR (cm−1) 3410, 2890, 1650, 1600, 1380 |
| 54 | 4-amino-5-(3-bromophenyl)-6-cyclohexyl-7-(6-dimethylamino-3-pyridinyl)pyrido [2,3-d]pyrimidine hydrochloride | MS m/z (M + H)+ 503, 505 (1Br); IR (cm−1) 3432, 3047, 2945, 1560, 1465, 1340 |
| 55 | 4-amino-5-(3-bromophenyl)-6-pentyl-7-(6-dimethylamino-3-pyridinyl)pyrido [2,3-d]pyrimidine hydrochloride | MS m/z (M + H)+ 491, 493 (1Br); IR (cm−1) 3437, 3025, 2952, 1550, 1450, 1320 |

What is claimed is:

1. A compound or a pharmaceutically acceptable salt or amide thereof having the formula (I)

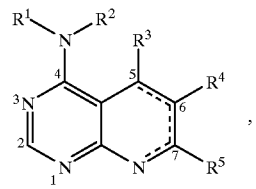

(I)

wherein $R^1$ and $R^2$ are independently H, loweralkyl, arylalkyl or acyl, or may be taken together with the nitrogen atom to which they are attached to form a 5-to-7 membered ring optionally containing 1–3 additional heteroatoms selected from N, O or S;

$R^3$ and $R^4$ are independently selected from loweralkyl, loweralkenyl, loweralkynyl, aryl, arylalkyl, heteroaryl, or a heterocyclic group, $R^5$ is selected from aryl, arylalkyl, heteroaryl or a heterocyclic group and the dashed lines indicate a double bond is optionally present with the proviso that the compound may not be a. 4-amino-5-(4-chorophenyl)-7-(4-nitrophenyl) pyridol[2,3-d]pyrimidine
b. 4-amino-5-(4-methoxyphenyl)-7-(4-nitrophenyl) pyridol[2,3-d]pyrimidine
c. 4-amino-5-(4-fluorophenyl)-7-(4-fluorophenyl) pyridol[2,3-d]pyrimidine
d. 4-amino-5-(4-chlorphenyl)-7-(4-fluorphenyl)pyridol [2,3-d]pyrimidine
e. 4-amino-5-phenyl-7-(4-aminophenyl)pyrido[2,3-d] pyrimidine
f. 4-amino-5-phenyl-7-(4-bromphenyl)pyrido[2,3-d] pyrimidine
g. 4-amino-5-(4-methoxyphenyl)-7-(4-aminophenyl) pyrido[2,3-d]pyrimidine
h. 4-amino-5-(4-methoxyphenyl)-7-(4-bromphenyl) pyrido[2,3-d]pyrimidine and
i. 4-amino-5,7-diphenylpyrido[2,3-d]pyrimidine.

2. A compound or a pharmaceutically acceptable salt or amide thereof having the formula (I)

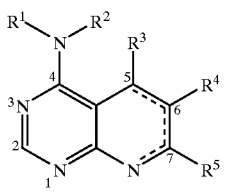

(I)

wherein:
$R^1$ and $R^2$ are independently selected from H, loweralkyl, aryl$C_1$–$C_6$alkyl, —C(O)$C_1$–$C_6$alkyl, —C(O)aryl, —C(O)heterocyclic or may join together with the nitrogen to which they are attached to from a 5–7 membered ring optionally containing 1–2 additional heteroatoms selected from O, N or S;
$R^3$, and $R^4$ are independently selected from the group consisting of:
  a. $C_1$–$C_6$alkyl,
  b. $C_2$–$C_6$alkenyl,
  c. $C_2$–$C_6$alkynyl,
  d. $C_3$–$C_8$cycloalkyl,
  e. heteroaryl$C_0$–$C_6$alkyl or substituted heteroaryl$C_0$–$C_6$alkyl,
  f. aryl$C_0$–$C_6$alkyl or substituted aryl$C_0$–$C_6$alkyl,
  g. heteroaryl$C_2$–$C_6$alkenyl or substituted heteroaryl$C_2$–$C_6$alkenyl,
  h. aryl$C_2$–$C_6$alkenyl or substituted aryl$C_2$–$C_6$alkenyl,
  i. heteroaryl$C_2$–$C_6$alkynyl or substituted heteroaryl$C_2$–$C_6$alkynyl,
  j. aryl$C_2$–$C_6$alkynyl or substituted aryl$C_2$–$C_6$alkynyl,
and R5 is independently selected from the group consisting of e–j above, and wherein the heteroaryl or aryl substituents are independently selected from: halogen, oxo, cyano$C_1$–$C_6$alkyl, heteroaryl$C_0$–$C_6$alkyl, heterocyclic$C_0$–$C_6$alkyl, $C_1$–$C_6$alkyloxy, $C_1$–$C_6$alkyloxy$C_1$–$C_6$alkyl, aryl$C_0$–$C_6$alkyl, aryl$C_1$–$C_6$alkyloxy, $R^6R^7$NC(O) cyano, $C_2$–$C_6$alkenyl, $C_2$–$C_6$alkynyl, $C_1$–$C_6$alkyl, $C_2$–$C_6$alkenyidialkylmalonyl, $CF_3$, HO—, $C_1$–$C_6$alkyloxy$C_1$–$C_6$alkyloxy, $C_1$–$C_6$alkylSO$_n$ wherein n is 1–2, $C_1$–$C_6$alkylthio, $C_1$–$C_6$alkylacryl, $CF_3O$, $CF_3$, $C_1$–$C_4$alkylenedioxy, $C_1$–$C_6$alkylacryl, $R^5R^6N$ (CO) $NR^5$, N-formyl(heterocyclic), $NO_2$, $NR^6R^7C_0$–$C_6$alkyl wherein $R^6$ and $R^7$ are independently selected from H, $C_1$–$C_6$alkyl, HC(O), $C_1$–$C_6$alkyloxy$C_1$–$C_6$alkyl, $C_1$–$C_6$alkyloxy, $C_1$–$C_6$alkyl$C(O)$, $CF_3C(O)$, $NR^8R^9C_1$–$C_6$alkyl phthalimido$C_1$–$C_6$C(O), $C_1$–$C_6$alkylSO$_n$ where n is 1–2, CN$C_1$–$C_6$alkyl, $R^8R^9NC(O)NR^8$—, heteroaryl, $NR^8R^9C_1$–$C_6$alkylC(O)$, $C_1$–$C_6$alkyloxycarbamido$C_1$–$C_6$alkyl,
wherein $R^8$ and $R^9$ are independently selected from those variables identified for $R^6$ and $R^7$ or
$R^6$ and $R^7$ or $R^8$ and $R^9$ may join together with the nitrogen atom to which they are attached to form a 5–7 membered unsubstituted or substituted ring optionally containing 1–3 additional heteroatoms selected from O, N or S wherein the substituents are selected from $C_1$–$C_6$alkyl with the provisio that the compound may not be
a. 4-amino-5-(4-chorophenyl)-7-(4-nitrophenyl) pyridol[2,3-d]pyrimidineb.
b. 4-amino-5-(4-methoxyphenyl)-7-(4-nitrophenyl) pyridol[2,3-d]pyrimidine
c. 4-amino-5-(4-fluorophenyl)-7-(4-fluorophenyl) pyridol[2,3-d]pyrimidine
d. 4-amino-5-(4-chlorphenyl)-7-(4-fluorphenyl)pyridol [2,3-d]pyrimidine
e. 4-amino-5-phenyl-7-(4-aminophenyl)pyrido[2,3-d] pyrimidine
f. 4-amino-5-phenyl-7-(4-bromphenyl)pyrido[2,3-d] pyrimidine
g. 4-amino-5-(4-methoxyphenyl)-7-(4-aminophenyl) pyrido[2,3-d]pyrimidine
h. 4-amino-5-(4-methoxyphenyl)-7-(4-bromphenyl) pyrido[2,3-d]pyrimidine and
i. 4-amino-5,7-diphenylpyrido[2,3-d]pyrimidine.

3. A compound of formula II

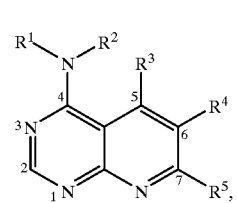

(II)

wherein
$R^1$ and $R^2$ are independently H, loweralkyl, arylalkyl or acyl, or may be taken together with the nitrogen atom to which they are attached to form a 5-to-7 membered ring optionally containing 1–3 additional heteroatoms selected from N, O or S; and
$R^3$ and $R^4$ are independently selected from loweralkyl, loweralkenyl, loweralkynyl, aryl, arylalkyl, heteroaryl, or a heterocyclic group,and $R^5$ is selected from aryl arylalky, heteroaryl or a heterocyclic with the provisio that the compound may not be
a. 4-amino-5-(4-chorophenyl)-7-(4-nitrophenyl) pyridol[2,3-d]pyrimidine
b. 4-amino-5-(4-methoxyphenyl)-7-(4-nitrophenyl) pyridol[2,3-d]pyrimidine
c. 4-amino-5-(4-fluorophenyl)-7-(4-fluorophenyl) pyridol[2,3-d]pyrimidine
d. 4-amino-5-(4-chlorphenyl)-7-(4-fluorphenyl)pyridol [2,3-d]pyrimidine
e. 4-amino-5-phenyl-7-(4-aminophenyl)pyrido[2,3-d] pyrimidine f. 4-amino-5-phenyl-7-(4-bromphenyl)pyrido[2,3-d]pyrimidine
g. 4-amino-5-(4-methoxyphenyl)-7-(4-aminophenyl)pyrido[2,3-d]pyrimidine
h. 4-amino-5-(4-methoxyphenyl)-7-(4-bromphenyl)pyrido[2,3-d]pyrimidine and
i. 4-amino-5.7-diphenylpyrido[2,3-d]pyrimidine.

4. A compound of formula II

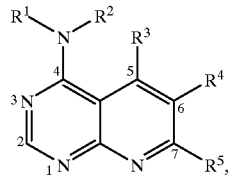

wherein:

$R^1$ and $R^2$ are independently selected from H, loweralkyl, aryl$C_1$–$C_6$alkyl, —C(O)$C_1$–$C_6$alkyl, —C(O)aryl, —C(O)heterocyclic or may join together with the nitrogen to which they are attached to from a 5–7 membered ring optionally containing 1–2 additional heteroatoms selected from O, N or S;

$R^3$ and $R^4$ are independently selected from the group consisting of:
a. $C_1$–$C_6$alkyl,
b. $C_2$–$C_6$alkenyl,
c. $C_2$–$C_6$alkynyl,
d. $C_3$–$C_8$cycloalkyl,
e. heteroaryl$C_0$–$C_6$alkyl or substituted heteroaryl$C_0$–$C_6$alkyl,
f. aryl$C_0$–$C_6$alkyl or substituted aryl$C_0$–$C_6$alkyl,
g. heteroaryl$C_2$–$C_6$alkenyl or substituted heteroaryl$C_2$–$C_6$alkenyl,
h. aryl$C_2$–$C_6$alkenyl or substituted aryl$C_2$–$C_6$alkenyl,
i. heteroaryl$C_2$–$C_6$alkynyl or substituted heteroaryl$C_2$–$C_6$alkynyl,
j. aryl$C_2$–$C_6$alkynyl or substituted aryl$C_2$–$C_6$alkynyl and $R^5$ is independently selected from the group consisting of e–j wherein the heteroaryl or aryl substituents are independently selected from
halogen, cyano$C_1$–$C_6$alkyl, heteroaryl, heterocyclic, $C_1$–$C_6$alkyloxy, $C_1$–$C_6$alkyloxy$C_1$–$C_6$alkyl, aryl$C_1$–$C_6$alkyl, $H_2NC_1$–$C_6$alkyl, aryl$C_1$–$C_6$alkyloxy, $H_2NC(O)$, cyano, $C_2$–$C_6$alkenyl, $C_2$–$C_6$alkynyl, $C_1$–$C_6$alkyl, $C_2$–$C_6$alkenyidialkylmalonyl, $CF_3$, HO—, $C_1$–$C_6$alkyloxy$C_1$–$C_6$alkyloxy, $SO_nC_1$–$C_6$alkyl wherein n is 1–3, $C_1$–$C_6$alkylthio, $C_1$–$C_6$alkylacryl, $CF_3O$, $CF_3$, $C_1$–$C_4$alkylenedioxy, $C_1$–$C_6$alkylacryl, $H_2N(CO)$ NH, N-formyl(heterocyclic), $NO_2$, $NR^6R^7C_0$–$C_6$alkyl,
wherein $R^6$ and $R^7$ are independently selected from H, $C_1$–$C_6$alkyl, HC(O), $C_1$–$C_6$alkyloxy$C_1$–$C_6$alkyl, $C_1$–$C_6$alkyloxy, $C_1$–$C_6$alkylC(O)$, $CF_3C(O)$, $NR^8R^9C_1$–$C_6$alkyl, phthalimido$C_1$–$C_6C(O)$, $CNC_1$–$C_6$alkyl, $H_3NC(O)NH$—, heteroaryl, $NR^8R^9C_1$–$C_6$alkylC(O)$, $C_1$–$C_6$alkyloxycarbamido$C_1$–$C_6$alkyl,
wherein $R^8$ and $R^9$ are independently selected from those variables identified for $R^6$ and $R^7$ or $R^6$ and $R^7$ or $R^8$ and $R^9$ may join together with the nitrogen atom to which they are attached to form a 5–7 membered unsubstituted or substituted ring optionally containing 1–3 additional heteroatoms selected from O, N or S wherein the substituents are selected from $C_1$–$C_6$alkyl, with the provisio that the compound may not be
a. 4-amino-5-(4-chorophenyl)-7-(4-nitrophenyl)pyridol[2,3-d]pyrimidine
b. 4-amino-5-(4-methoxyphenyl)-7-(4-nitrophenyl)pyridol[2,3-d]pyrimidine
c. 4-amino-5-(4-fluorophenyl)-7-(4-fluorophenyl)pyridol[2,3-d]pyrimidine
d. 4-amino-5-(4-chlorphenyl)-7-(4-fluorphenyl)pyridol[2,3-d]pyrimidine
e. 4-amino-5-phenyl-7-(4-aminophenyl)pyrido[2,3-d]pyrimidine
f. 4-amino-5-phenyl-7-(4-bromphenyl)pyrido[2,3-d]pyrimidine
g. 4-amino-5-(4-methoxyphenyl)-7-(4-aminophenyl)pyrido[2,3-d]pyrimidine
h. 4-amino-5-(4-methoxyphenol)-7-(4-bromphenyl)pyrido[2,3-d]pyrimidine and
i. 4-amino-5,7-diphenylpyrido[2,3-d]pyrimidine.

5. A compound according to claim 4 wherein $R^3$, $R^4$ and $R^5$ are independently selected from phenyl; thiophen-2-yl; 1-methyl-2-oxobenzoxazolin-5-yl; 2-(dimethylamino)-5-pyrimidinyl; 2-(N-formyl-N-methyl amino)-3-pyrimidinyl; 2-(N-(2-methoxyethyl)-N-methylamino)-5-pyrimidinyl; 5-dimethylamino-2-pyridinyl; 5-(N-(2-methoxyethyl)-N-5 methylamino)-2-pyridinyl; 2-(N-methylamino)-5-pyrimidinyl; 2-(1-morpholinyl)-5-pyrimidinyl; 2-(1-pyrrolidinyl)-5-pyrimidinyl; 2-dimethylamino-5-pyrimidinyl; 2-furanyl; 2-oxobenzoxazolin-5-yl; 2-pyridyl; 3-(dimethylamino)phenyl; 3-amnino4-methoxyphenyl; 3-bromo-4-(dimethylamino)phenyl; 3-methoxyphenyl; 3-methyl-4-(N-acetyl-N-methylamino)phenyl; 3-methyl-4-(N-formyl-N-methylamino)phenyl; 3-methyl4-(N-methyl-N-(trifluoroacetyl)amino)phenyl; 3-methyl-4-(N-methylamino)phenyl; 3-methyl-4-pyrrollidinylphenyl; 3-pyridyl; 3,4-dichlorophenyl; 3,4-methylenedioxyphenyl; 3,4,5-trimethoxyphenyl; 4-(acetylamino)phenyl; 4-(dimethylamino)-3-fluorophenyl; 4-(dimethylamino)phenyl; 4-(imidazol-1-yl)phenyl; 4-(methylthio)phenyl; 4-(morpholinyl)phenyl; 4-(N-(2-(dimethylamino)ethyl)amino)phenyl; 4-(N-(2-methoxyethyl)amino)phenyl; 4-(N-acetyl-N-methylamino)phenyl; 4-(N-ethyl-N-formylamino)phenyl; 4-(N-ethylamino)phenyl; 4-(N-formyl-N-(2-methoxyethyl)amino)phenyl; 4-(N-isopropylamino)phenyl; 4-(N-methyl-N-((2-dimethylamino)ethyl)amino)phenyl; 4-(N-methyl-N-(2-(N-phthalimidyl)acetyl)amino)phenyl; 4-(N-methyl-N-(2-cyano)ethylamino)phenyl; 4-(N-methyl-N-(2-methoxyethyl)amino)phenyl; 4-(N-methyl-N-(3-methoxy)propionylamino)phenyl; 4-(N-methyl-N-acetylamino)phenyl; 4-(N-methyl-N-formylamino)phenyl; 4-(N-methyl-N-trifluoroacetylamino)phenyl; 4-(N-morpholinyl)phenyl; 4-(thiophen-2-yl)phenyl; 4-(ureido)phenyl; 4-(2-(dimethylamino)acetylamino)phenyl; 4-(2-(2-methoxy)acetylamino)ethyl)amino)phenyl; 4-(2-methoxy)ethoxyphenyl; 4-(2-oxo-1-oxazolidinyl)phenyl; 4-(4-methoxy-2-butyl)phenyl; 4-(4-methylpiperidinyl)phenyl; 4-(5-pyrimidinyl)phenyl; 4-aminophenyl; 4-bromophenyl; 4-butoxyphenyl; 4-carboxamidophenyl; 4-chlorophenyl; 4-cyanophenyl; 4-diethylaminophenyl; 4-diethylmalonylallylphenyl); 4-dimethylaminophenyl; 4-ethoxyphenyl; 4-ethylphenyl; 4-fluorophenyl; 4-hydroxyphenyl; 4-imidazolylphenyl; 4-iodophenyl; 4-isopropylphenyl; 4-methoxyphenyl) 4-methylaminophenyl; 4-methylsulfonylphenyl;

4-morpholinylphenyl; 4-N-(2-(dimethylamino)ethyl)-N-formylamino)phenyl; 4-N-(3-methoxypropionyl)-N-isopropyl-amino)phenyl; 4-N-ethyl-N-(2-methoxyethyl) amino)phenyl; 4-N-formylpiperidinylphenyl; 4-nitrophenyl; 4-piperidinylphenyl; 4-pyridylphenyl; 4-pyrrolidinylphenyl; 4-t-butylacrylphenyl; 5-(dimethylamino)thiophen-2-yl; 5-amino-2-pyridyl; 5-dimethylamino-2-pyrazinyl; 3-dimethylaminopyridazin-6-yl; 5-dimethylamino-2-pyridyl; 5-pyrimidinylphenyl; 6-(N-methyl-N-formylamino)-3-pyridinyl; 6-(N-methyl-N-(2-methoxyethyl)amino)-3-pyridinyl; 6-(2-oxo-oxazolidinyl)-3-pyridinyl; 6-dimethylamino-3-pyridinyl; 6-imidazolyl-3-pyridinyl; 6-morpholinyl-3-pyridinyl; 6-pyrrolidinyl-3-pyridinyl; (2-propyl)-3-pyridinyl; and (4-formylamino) phenyl; (thiophen-2-yl)methyl; (thiophen-3-yl)methyl; butyl; cycloheptyl; pentyl; thiophen-2-yl; 1-(3-bromophenyl)ethyl; 2-(N-phenylmethoxycarbonyl) aminophenyl; 2-(3-bromophenyl)ethyl; 2-(3-cyanophenyl) methyl; 2-(4-bromophenyl)ethyl; 2-(5-chloro-2-(thiophen-3-yl)phenyl; 2-bromophenyl; 2-furanyl; 2-methylpropyl; 2-phenylethyl; phenylmethyl; 2,3-dimethoxyphenyl; 2,3-methylenedioxyphenyl; 3-(furan-2-yl)phenyl; 3-(thiophen-2-yl)phenyl; 3-(2-pyridyl)phenyl; 3-(3-methoxybenzyl) phenyl; 3-(amino)propynyl; 3-benzyloxyphenyl; 3-bromo-4-fluorophenyl; 3-bromo-5-iodophenyl; 3-bromo-5-methoxyphenyl; 3-bromophenyl; 3-bromophenylmethyl; 3-carboxamidophenyl; 3-chlorophenyl; 3-cyanophenyl; 3-diethylmalonylallylphenyl; 3-dimethylaminophenyl; 3-ethoxyphenyl; 3-fluoro-5-trifluoromethylphenyl; 3-fluorophenyl; 3-hydroxyphenyl; 3-iodophenyl; 3-methoxyethyoxyphenyl; 3-methoxyphenyl; 3-methylphenyl; 3-methylsulfonylphenyl; 3-methylthiophenyl; 3-t-butylacrylphenyl; 3-trifloromethyoxyphenyl; 3-trifluoromethylphenyl; 3-vinylpyridinylphenyl; 3,4-dichlorophenyl; 3,4-dimethoxyphenyl; 3,4-methylenedioxyphenyl; 3,4,5-trimethoxyphenyl; 3,5-di(trifluoromethyl)phenyl; 3,5-dibromophenyl; 3,5-dichlorophenyl; 3,5-dimethoxyphenyl; 3,5-dimethylphenyl; 4-(2-propyl)phenyl; 4-(2-propyl) oxyphenyl; 4benzyloxyphenyl; 4-bromophenyl; 4-bromothiophen-2-yl; 4-butoxyphenyl; 4-dimethylaminophenyl; 4-fluoro-3-trifluoromethylphenyl; 4-methoxyphenyl; 4-neopentylphenyl; 4-phenoxyphenyl; 5-bromothiophen-2-yl; cyclohexyl; cyclopropyl; hexyl; methyl; phenyl; (2-bromo-5-chlorophenyl)methyl; (2-bromophenyl)methyl; 6-cyclopropylmethylamino-3-pyridinyl; and (5-chloro-2-(3-methoxyphenyl)phenyl) methyl.

6. A compound according to claim 5 wherein $R^5$ is selected from the group consisting of: 4-(dimethylamino) phenyl; 5-dimethylamino-2-pyridinyl; 5-methoxy-2-pyridinyl; 4-methoxyphenyl; 5-methylthiophen-2-yl; 4-(N-methyl-N-(2-methoxyethyl)amino)phenyl; and thiophen-2-yl.

7. A compound according to claim 5 wherein $R^4$ is selected from the group consisting of: ethoxycarbonylmethyl; ethyl; 3-fluorophenyl; 3-fluoro-methylphenyl; 3,4-dimethoxyphenyl; 3-methoxyphenyl; 4-methoxyphenyl; pentyl; phenyl; 3-(2-propyl)phenyl; and 4-(2-propyl)phenyl.

8. A compound according to claim 5 wherein $R^3$ is selected from the group consisting of: 3-bromophenyl; 3-bromo-4-fluorophenyl; 4-bromothiophen-2-yl; 3-chlorophenyl; 3,4-dimethoxyphenyl; 3-fluorophenyl; 3-fluoro-4methylphenyl; 4-(2-propyl)phenyl; and 3-trifluoromethyl4-fluorophenyl.

9. A compound according to claim 2 which is
4-amino-5-(3-bromo-4-fluorophenyl)-6-pentyl-7-(4-(dimethylamino)phenyl)pyrido[2,3-d]pyrimidine;
4-amino-5-(3-bromo4-fuorophenyl)-6-pentyl-7-(thiophen-2-yl)pyrido[2,3-d]pyrimidine;
4-amino-5-(3-bromophenyl)-6-(4-methoxyphenyl)-7-(4-methoxyphenyl)pyrido[2,3-d]pyrimidine;
4-amino-5-(3-bromophenyl)-6-ethyl-7-(thiophen-2-yl) pyrido[2,3-d]pyrimidine;
4-amino-5-(3-bromophenyl)-6-pentyl-7-(thiophen-2-yl) pyrido[2,3-d]pyrimidine;
4-amino-5-(3-bromophenyl)-6-(3,4-dimethoxyphenyl)-7-(thiophen-2-yl)pyrido[2,3-d]pyrimidine;
4-amino-5-(3-bromophenyl)-6-(4-(2-propyl)phenyl)-7-(4-(dimethylamino)phenyl)pyrido[2,3-d]pyrimidine;
4-amino-5-(3-bromophenyl)-6-ethoxycarbonylmethyl-7-(thiophen-2-yl)pyrido[2,3-d]pyrimidine;
4-amino-5-(3-bromophenyl)-6-(3-methoxyphenylmethyl)-7-(thiophen-2-yl)pyrido[2,3-d]pyrimidine;
4-amino-5-(3-bromophenyl)-6-(3,4-dimethoxyphenyl)-7-(4-(dimethylamino)phenyl)pyrido[2,3-d]pyrimidine;
4-amino-5-(4-bromothiophen-2-yl)-6-(3,4-dimethoxyphenyl)-7-(thiophen-2-yl)pyrido[2,3-d] pyrimidine;
4-amino-5-(3-chlorophenyl)-6-(3,4-dimethoxyphenyl)-7-(thiophen-2-yl)pyrido[2,3-d]pyrimidine;
4-amino-5-(3-trifluoromethyl-4-fluorophenyl)-6-(3,4-dimethoxyphenyl)-7-(thiophen-2-yl)pyrido[2,3-d] pyrimidine;
4-amino-5-(3-chlorophenyl)-6-(3,4-dimethoxyphenyl)-7-(4-(dimethylamino)phenyl)pyrido[2,3-d]pyrimidine;
4-amino-5-(3-trifluoromethyl-4-fluorophenyl)-6-(3,4-dimethoxyphenyl)-7-(4-(dimethylamino)phenyl)pyrido [2,3-d]pyrimidine;
4-amino-5-(3-chlorophenyl)-6-(3,4-dimethoxyphenyl)-7-(5-methylthiophen-2-yl)pyrido[2,3-d]pyrimidine;
4-amino-5-(4-bromothiophen-2-yl)-6-(3,4-dimethoxyphenyl)-7-(5-methylthiophen-2-yl)pyrido[2,3-d]pyrimidine;
4-amino-5-(4-bromothiophen-2-yl)-6-(3,4-dimethoxyphenyl)-7-(4-(dimethylamino)phenyl)pyrido [2,3-d]pyrimidine;
4-amino-5-(4-bromothiophen-2-yl)-6-(3,4-dimethoxyphenyl)-7-(4-(N-methyl-N-(2-methoxyethyl) amino)phenyl)pyrido[2,3-d]pyrimidine;
4-amino-5-phenyl-6-(3,4-dimethoxyphenyl)-7-(4-(N-methyl-N-(2-methoxyethyl)amino)phenyl)pyrido[2,3-d] pyrimidine;
4-amino-5-(3-chlorophenyl)-6-(3,4-dimethoxyphenyl)-7-(4-(N-methyl-N-(2-methoxyethyl)amino)phenyl)pyrido [2,3-d]pyrimidine;
4-amino-5-phenyl-6-(3,4-dimethoxyphenyl)-7-(5-methoxy-2-pyridinyl)pyrido[2,3-d]pyrimidine;
4-amino-5-(3-chlorophenyl)-6-(3,4-dimethoxyphenyl)-7-(5-methoxy-2-pyridinyl)pyrido[2,3-d]pyrimidine;
4-amino -5-(3-chlorophenyl)-6-(3,4-dimethoxyphenyl)-7-(5-dimethylamino-2-pyridinyl)pyrido[2,3-d]pyrimidine;
4-amino-5,6-bis(4-(2-propyl)phenyl-7-(4-dimethylaminophenyl)pyrido[2,3-d]pyrimidine;
4-amino-5,6-diphenyl-7-(4-(N-methyl-N-(2-methoxyethyl) amino)phenyl)pyrido[2,3-d]pyrimidine;
4-amino-5,6-diphenyl-7-(4-dimethylaminophenyl)pyrido[2,3-d]pyrimidine;
4-amino-5,6-bis(3-fluorophenyl)-7-(4-dimethylaminophenyl)pyrido[2,3-d]pyrimidine;
4-amino-5,6-bis(3,4-dimethoxyphenyl)-7-(4-dimethylaminophenyl)pyrido[2,3-d]pyrimidine;
4-amino-5,6-bis(3-fluoro-4-methylphenyl)-7-(4-dimethylaminophenyl)pyrido[2,3-d]pyrimidine;
4-amino-5,6-bis(3-fluoro-4-methylphenyl)-7-(thiophen-2-yl)pyrido[2,3-d]pyrimidine;

4-amino-5,6-diphenyl-7-(thiophen-2-yl)pyrido[2,3-d]pyrimidine;
4-amino-5,6-diphenyl-7-(5-dimethylamino-2-pyridinyl)pyrido[2,3-d]pyrimidine;
4-amino-5-phenyl-6-(3,4-dimethoxyphenyl)-7-(5-(dimethylamino)pyridin-2-yl)pyrido[2,3-d]pyrimidine;
4-amino-5-(3-chlorophenyl)-6-(3,4-dimethoxyphenyl)-7-(5-N-(2-methoxyethyl)-N-methylamino)-2-pyridinyl)pyrido[2,3-d]pyrimidine;
4-amino-5-(3-chlorophenyl)-6-phenyl-7-(4-dimethylamino-2-pyridinyl)pyrido[2,3-d]pyrimidine;
4-amino-5-(4-bromothiophen-2-yl)-6-phenyl-7-(5-dimethylamino-2-pyridinyl)pyrido[2,3-d]pyrimidine;
4-amino-5-(3-bromophenyl)-6-phenyl-7-(6-dimethylamino-3-pyridinyl)pyrido[2,3-d]pyrimidine;
4-amino-5-(3-bromophenyl)-6-(4fluorophenyl)-7-(6-morpholinyl-3-pyridinyl)pyrido[2,3-d]pyrimidine;
4-amino-5-phenyl-6-phenyl-7-(6-morpholinyl-3-pyridinyl)pyrido[2,3-d]pyrimidine;
4-amino-5-(3-bromophenyl)-6-phenyl-7-(6-morpholinyl-3-pyridinyl)pyrido[2,3-d]pyrimidine;
4-amino-5-phenyl-6-phenyl-7-(6-(N-methyl-N-(2-methoxyethyl)amino)-3-pyridinyl)pyrido[2,3-d]pyrimidine;
4-amino-5-(4bromothienyl)-6-phenyl-7-(6-(N-methyl-N-(2-methoxyethyl)amino)-3-pyridinyl)pyrido[2,3-d]pyrimidine;
4amino-5-(4bromothienyl)-6-cyclopropyl-7-(6-dimethylamino-3-pyridinyl)pyrido[2,3-d]pyrimidine;
4-amino-5-(4bromothienyl)-6-(4fluorophenyl)-7-(6-morpholiny-1-3-pyridinyl)pyrido[2,3-d]pyrimidine;
4-amino-5-(3-bromophenyl)-6-phenyl-7-(6-cyclopropylmethylamino-3-pyridinyl)pyrido[2,3-d]pyrimidine;
4-amino-5-phenyl-6-phenyl-7-(6-cyclopropylmethylanino-3-pyridinyl)pyrido[2,3-d]pyrimidine;
4-amino-5-(3-bromophenyl)-6-(-fluorophenyl)-7-(6-morpholinyl-3-pyridinyl)pyrido[2,3-d]pyrimidine;
4-amino-5-(3-chlorophenyl)-6-heptyl-7-(6-morpholinyl-3-pyridinyl)pyrido[2,3-d]pyrimidine;
4-amino-5-phenyl-6-phenylmethyl-7-(6-morpholinyl-3-pyridinyl)pyrido[2,3-d]pyrimidine;
4-amino-5-(4bromothienyl)-6-heptyl-7-(6-morpholinyl-3-pyridinyl)pyrido[2,3-d]pyrimidine;
4-amino-5-(4bromothienyl)-6-(1-methylethyl)-7-(6-morpholinyl-3-pyridinyl)pyrido[2,3-d]pyrmidine;
4-amino-5-(4bromothienyl)-6-phenylmethyl-7-(6-morpholinyl-3-pyridinyl)pyrido[2,3-d]pyrimidine;
4-amino-5-(3-bromophenyl)-6-cyclohexyl-7-(6-dimethylamnino-3-pyridinyl)pyrido[2,3-d]pyrimidine;
or
4-amino-5-(3-bromophenyl)-6-pentyl-7-(6-dimethylanino-3-pyridinyl)pyrido[2,3-d]pyrimidine.

10. A method for inhibiting adenosine kinase by administering a compound according to claim 1 or 3.

11. A pharmaceutical composition comprising a therapeutically effective amount of a compound according to claim 1 or 3 in combination with a pharmaceutically acceptable carrier.

12. A method of treating ischemia, neurological disorders, nociperception, inflammation, immunosuppression, gastrointestinal disfunctions, diabetes and sepsis in a mammal in need of such treatment, comprising administering to the mammal a therapeutically effective amount of a compound according to claim 1 or 3.

13. A method according to claim 12 wherein the method consists of treating cerebral ischemia, myocardial ischemia, angina, coronary artery bypass graft surgery, percutaneous transluminal angioplasty, stroke, thrombotic and embolic conditions, epilepsy, anxiety, schizophrenia, pain perception, neuropathic pain, visceral pain, arthritis, sepsis, diabetes and abnormal gastrointestinal motility.

14. A method for inhibiting adenosine kinase which comprises administering to a mammal in need of such treatment a therapeutically effective amount of the compound of the formula (II)

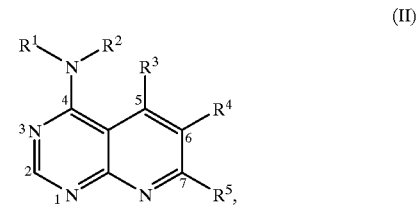

(II)

wherein $R^1$ and $R^2$ are independently H, loweralkyl, arylalkyl or acyl, or may be taken together with the nitrogen atom to which they are attached to form a 5-to-7 membered ring optionally containing 1–3 additional heteroatoms selected from N, O or S; and $R^3$ and $R^4$ are independently selected from loweralkyl, loweralkenyl, loweralkynyl, aryl, arylalkyl, heteroaryl, or a heterocyclic group and $R^5$ is selected from aryl, arylalkyl, heteroaryl or a heterocyclic group.

15. A method for the treatment of ischemia, neurological disorders, nociperception, inflammation, immunosuppression, gastrointestinal disfunctions, diabetes and sepsis in a mammal in need of such treatment, which comprises administering to said mammal a therapeutically effective amount of a compound of the formula (II)

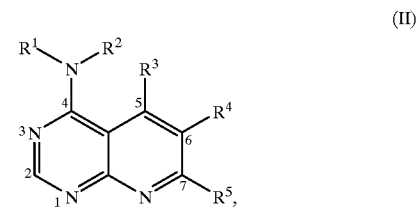

(II)

wherein $R^1$ and $R^2$ are independently H, loweralkyl, arylalkyl or acyl, or may be taken together with the nitrogen atom to which they are attached to form a 5-to-7 membered ring optionally containing 1–3 additional heteroatoms selected from N, O or S; and $R^3$ and $R^4$ are independently selected from loweralkyl, loweralkenyl, loweralkynyl, aryl, arylalkyl, heteroaryl, or a heterocyclic group and $R^5$ is selected from aryl, arylalkyl, heteroaryl or a heterocyclic group.

16. A method for the treatment of cerebral ischemia, myocardial ischemia, angina, coronary artery bypass graft surgery, percutaneous transluminal angioplasty, stroke, thrombotic and embolic conditions, epilepsy, anxiety, schizophrenia, pain perception, neuropathic pain, visceral pain, arthritis, sepsis, diabetes and abnormal gastrointestinal motility in a mammal which comprises administering to said mammal in need of such treatment, a therapeutically effective amount of a compound of the formula (II)

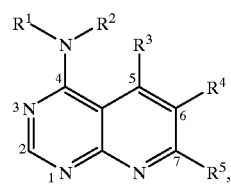
(II)

wherein $R^1$ and $R^2$ are independently H, loweralkyl, arylalkyl or acyl, or may be taken together with the nitrogen atom to which they are attached to form a 5-to-7 membered ring optionally containing 1–3 additional heteroatoms selected from N, O or S; and $R^3$ and $R^4$ are independently selected from loweralkyl, loweralkenyl, loweralkynyl, aryl, arylalkyl, heteroaryl, or a heterocyclic group and $R^5$ is selected from aryl, arylalkyl, heteroaryl or a heterocyclic group.

* * * * *